US007630837B2

(12) United States Patent
Eyre et al.

(10) Patent No.: US 7,630,837 B2
(45) Date of Patent: Dec. 8, 2009

(54) REAL-TIME GENE QUANTIFICATION WITH INTERNAL STANDARDS

(75) Inventors: David J. Eyre, Salt Lake City, UT (US); Randy P. Rasmussen, Salt Lake City, UT (US); Brian E. Caplin, Salt Lake City, UT (US); Wade R. Stevenson, West Jordan, UT (US); Deepika Marine deSilva, Salt Lake City, UT (US)

(73) Assignees: Idaho Technology, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 658 days.

(21) Appl. No.: 10/230,489

(22) Filed: Aug. 29, 2002

(65) Prior Publication Data

US 2003/0104438 A1 Jun. 5, 2003

Related U.S. Application Data

(60) Provisional application No. 60/316,614, filed on Aug. 31, 2001.

(51) Int. Cl.
*G01N 33/48* (2006.01)
*C12P 19/34* (2006.01)
*C12Q 1/68* (2006.01)
*C07H 21/02* (2006.01)
*C07H 21/04* (2006.01)

(52) U.S. Cl. .............................. 702/19; 702/20; 702/27; 435/6; 435/91.1; 435/91.2; 536/23.1; 536/24.3; 536/24.33

(58) Field of Classification Search ................. 435/91.2; 702/20
See application file for complete search history.

(56) References Cited

U.S. PATENT DOCUMENTS

| | | |
|---|---|---|
| 5,118,801 A | 6/1992 | Lizardi et al. |
| 5,219,727 A | 6/1993 | Wang et al. |
| 5,273,632 A | 12/1993 | Stockham et al. |
| 5,346,306 A | 9/1994 | Reading et al. |
| 5,436,149 A | 7/1995 | Barnes |
| 5,455,175 A | 10/1995 | Wittwer et al. |
| 5,476,774 A | 12/1995 | Wang et al. |
| 5,748,491 A | 5/1998 | Allison et al. |
| 5,906,919 A | 5/1999 | Garini et al. |
| 5,912,165 A | 6/1999 | Cabib et al. |
| 5,985,120 A | 11/1999 | Cholli et al. |
| 6,054,268 A | 4/2000 | Perlin |
| 6,066,459 A | 5/2000 | Garini et al. |
| 6,174,670 B1 | 1/2001 | Wittwer et al. |
| 6,221,600 B1 | 4/2001 | MacLeod et al. |
| 6,268,131 B1 | 7/2001 | Kang et al. |
| 6,387,621 B1 | 5/2002 | Wittwer |
| 2001/0016323 A1 | 8/2001 | Parkhurst et al. |

FOREIGN PATENT DOCUMENTS

EP 0 567 622 B1 11/1992

OTHER PUBLICATIONS

"Quantification of HER2/neu Gene Amplification by Competitive PCR Using Fluorescent Melting Curve Analysis," Elaine Lyon et al., *Clinical Chemistry*, 47:5, 844-851(2001).
"Homogeneous Multiplex Genotyping of Hemochromatosis Mutations With Fluorescent Hybridization Probes," Philip S. Bernard et al., *American Journal of Pathology*, vol. 153, No. 4, Oct. 1998, 1055-1061.
Product Differentiation by Analysis of DNA Melting Curves During the Polymerase Chain Reaction, Kirk M. Ririe et al., *Analytical Biochemistry*, 245, 154-160 (1997).
"Quantification of PCR by Continuous Flouoresence Monitoring of a Double Strand DNA Specific Binding Dye," Randy Rasmussen et al., *Biochemica* No. 2 [1998].
Higuchi et al., "Simultaneous Amplification and Detection of Specific DNA Sequences," *Biotechnology* 10, pp. 413-417, (1992).
Wittwer, C.T. et al., "Continuous Fluorescence Monitoring of Rapid Cycle DNA Amplification," *Bio Techniques* 22, pp. 130-138 (1997).
Bernard, P.S., et al., "Integrated Amplification and Detection of the C677T Point Mutation in the Methylenetetrahydrofolate Reductase Gene By Fluorescence Resonance Energy Transfer and Probe Melting Curves," *Analytical Biochemistry*, 255, pp. 101-107, (1998).
Crocket, "Fluorescein-Labeled Oligonucleotides for Real-Time PCR: Using the Inherent Quenching of Deoxyguanosine Nucleotides," *Analytical Biochemistry*, 290; 89-97, (2001).

*Primary Examiner*—Shubo (Joe) Zhou
(74) *Attorney, Agent, or Firm*—Barnes & Thornburg LLP

(57) ABSTRACT

The present invention is directed to a nucleic acid quantification kit and method for determining the initial concentration or mass fraction of a target nucleic acid present in a sample. Illustrative embodiments include real-time competitive quantitative polymerase chain reaction (PCR) to determine the copy number or mass fraction of a target nucleic acid sequence in a sample and use of a thermodynamically based signal processing algorithm, with or without PCR, to provide mass fraction information.

16 Claims, 21 Drawing Sheets

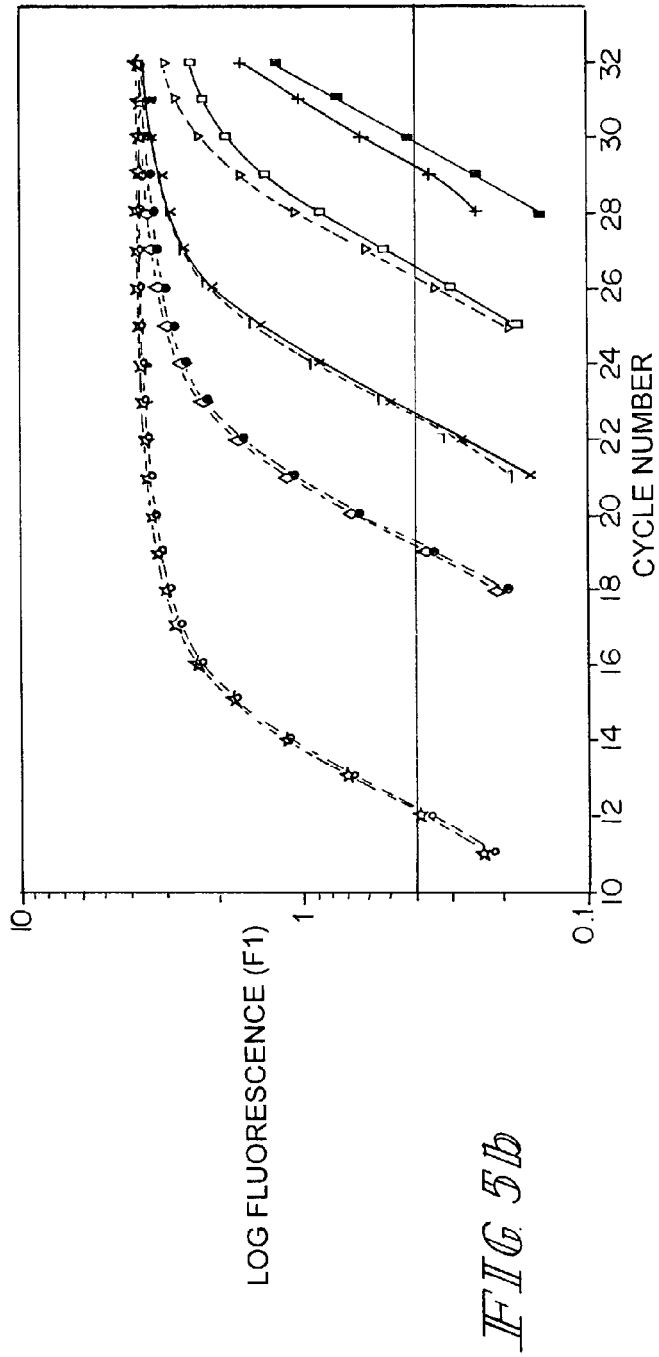
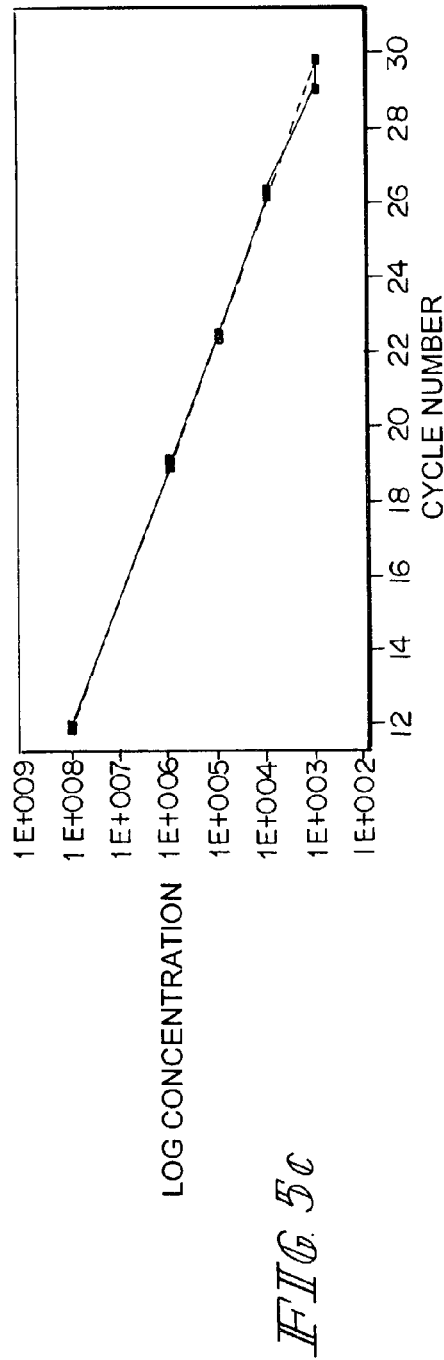
FIG. 5b
FIG. 5c

PANEL A

PANEL B

REAL-TIME GENE QUANTIFICATION WITH INTERNAL STANDARDS

This application claims the benefit of U.S. Provisional Application No. 60/316,614, filed Aug. 31, 2001, which is incorporated by reference herein in its entirety.

BACKGROUND

The polymerase chain reaction (PCR) is a technique of synthesizing large quantities of a preselected DNA segment. The technique is fundamental to molecular biology and is the first practical molecular technique for the clinical laboratory. PCR is achieved by separating the DNA into its two complementary strands, binding a primer to each single strand at the end of the given DNA segment where synthesis will start, and adding a DNA polymerase to synthesize the complementary strand on each single strand having a primer bound thereto. The process is repeated until a sufficient number of copies of the selected DNA segment have been synthesized.

During a typical PCR reaction, double stranded DNA is separated into its single strands by raising the temperature of the DNA containing sample to a denaturing temperature where the two DNA strands separate (i.e. the "melting temperature of the DNA") and then the sample is cooled to a lower temperature that allows the specific primers to attach (anneal), and replication to occur (extend). In illustrated embodiments, a thermostable polymerase is utilized in the polymerase chain reaction, such as Taq DNA Polymerase and derivatives thereof, including the Stoffel fragment of Taq DNA polymerase and KlenTaq1 polymerase (a 5'-exonuclease deficient variant of Taq polymerase—see U.S. Pat. No. 5,436,149).

The years 1991 to 1998 have seen a 10 fold increase in the number of papers using quantitative PCR methods. One of the major reasons for this increased use of quantitative PCR derives from the fact that PCR has a sensitivity five orders of magnitude better than the best blotting procedures. This sensitivity makes PCR as a quantitative tool highly desirable. However, the use of a system undergoing exponential amplification is not ideally suited to quantification. Small differences between sample sizes can become huge difference in results when they are amplified through forty doublings.

Kinetic PCR

A typical PCR reaction profile can be thought of has having three segments: an early lag phase, an exponential growth phase, and a plateau. The lag phase is mainly a reflection of the sensitivity of the instrument and the background signal of the probe system used to detect the PCR product. The exponential growth phase begins when sufficient product has accumulated to be detected by the instrument. During this "log" phase the amplification course is described by the equation $T_n = T_o(E)_n$, where $T_n$ is the amount of target sequence at cycle n, $T_o$ is the initial amount of target, and E is the efficiency of amplification. Finally, in the plateau phase, the amplification efficiency drops off extremely rapidly. Product competes more and more effectively with primers for annealing and the amount of enzyme becomes limiting. The exponential equation no longer holds in the plateau phase.

Most of the quantitative information is found in the exponential cycles, but the exponential cycles typically comprise only 4 or 5 cycles out of 40. With traditional PCR methods, finding these informative cycles requires that the reaction be split into multiple reaction tubes that are assayed for PCR product after varying numbers of cycles. This requires either assaying many tubes, or a fairly good idea of the answer before the experiment is begun. Once the position of the exponential phase is determined, the experimental phase can be compared to known standards and the copy number can be calculated.

Competitive Quantitative PCR

Competitive quantitative PCR methods were developed to attempt to overcome difficulties associated with finding the exponential phase of the reaction and to obtain greater precision. A competitor sequence is constructed that is amplified using the same primers as are used to amplify the target sequence. Competitor and target are differentiated, usually by length or internal sequence, and the relative amount of competitor and target are measured after amplification. If the target and the competitor are amplified with equal efficiency, then their ratio at the end of the reaction will be the same as the ratio had been at the beginning. This holds true even into the plateau phase as long as both decline in efficiency at the same rate. Thus, finding the exponential region is no longer a problem. Providing standards in the same tubes with the unknown targets allows for additional control not possible with kinetic methods. For example, adding the competitor before mRNA purification would control for variations in sample preparation and reverse transcription.

The use of currently available competitive PCR techniques continues to suffer from several deficiencies. Firstly, the competitor sequence must be constructed to be as similar as possible to the target sequence with regard to the efficiency of amplification, yet the two sequences must be distinguishable from one another. If the competitor is too close in sequence to the target, heteroduplexes form during the PCR that skew the ratio of the product to the template.

In addition, competitor must be added to the unknown sample at a concentration approximating that of the target. If one product reaches plateau before the other rises above background, no quantitative information can be obtained from that sample. Usually an unknown sample is split and mixed with multiple concentrations of competitor.

Other concerns have been raised regarding competitive quantification methods. A common criticism is that despite all efforts, the target and the competitor together in a sample may be amplified at different efficiencies, even if target and competitor are amplified at the same efficiencies when amplified separately (the obvious control). When the target and competitor are combined in one vessel and the reagents are limiting, the efficiencies of the two amplification reactions may change at different rates. Length differences between target and competitor are of most concern here as the longer product may compete more effectively with the primers and may be more affected by reagent limitations. Both of these concerns could be addressed by making the target and competitor sufficiently alike, if it were not for the problem of forming heteroduplexes during the PCR reaction.

Real-Time Quantitative PCR

Developments in instrumentation have now made real-time monitoring of PCR reactions possible and thus have made the problem of finding the log phase of the reaction trivial.

Thermocycling may be carried out using standard techniques known to those skilled in the art, including the use of rapid cycling PCR. Rapid cycling techniques are made possible by the use of high surface area-to-volume sample containers such as capillary tubes. The use of high surface area-to-volume sample containers allows for a rapid temperature response and temperature homogeneity throughout the biological sample. Improved temperature homogeneity also increases the precision of any analytical technique used to monitor PCR during amplification.

In accordance with an illustrated embodiment of the present invention, amplification of a nucleic acid sequence is conducted by thermal cycling the nucleic acid sequence in the presence of a thermostable DNA polymerase using the device and techniques described in U.S. Pat. No. 5,455,175, the disclosure of which is expressly incorporated herein. In accordance with the present invention, PCR amplification of one or more targeted regions of a DNA sample is conducted while the reaction is monitored by fluorescence.

The first use of fluorescence monitoring at each cycle for quantitative PCR was developed by Higuchi et al., "Simultaneous Amplification and Detection of Specific DNA Sequences," Bio. Technology, 10:413-417, 1992, and used ethidium bromide as the fluorescent entity. Fluorescence was acquired once per cycle for a relative measure of product concentration. The cycle where observable fluorescence first appeared above the background fluorescence (the threshold) correlated with the starting copy number, thus allowing the construction of a standard curve. A probe-based fluorescence detection system dependent on the 5'-exonuclease activity of the polymerase soon followed. This improved the real-time kinetic method by adding sequence specific detection.

Alternatively, PCR amplification of one or more targeted regions of a DNA sample can be conducted in the presence of fluorescently labeled hybridization probes, wherein the probes are synthesized to hybridize to a specific locus present in a target amplified region of the DNA. In an illustrated embodiment, the hybridization probe system comprises two oligonucleotide probes that hybridize to adjacent regions of a DNA sequence wherein each oligonucleotide probe is labeled with a respective member of a fluorescent energy transfer pair. In this embodiment, the presence of the target nucleic acid sequence in a biological sample is detected by measuring fluorescent energy transfer between the two labeled oligonucleotides.

These instrumentation and fluorescent monitoring techniques have made kinetic PCR significantly easier than traditional competitive PCR. More particularly, real-time PCR has greatly improved the ease, accuracy, and precision of quantitative PCR by allowing observation of the PCR product concentration at every cycle. In illustrated embodiments of the present invention, PCR reactions are conducted using the LIGHTCYCLER® (Roche Diagnostics), a real-time PCR instrument that combines a rapid thermal cycler with a fluorimeter. Through the use of this device, the PCR product is detected with fluorescence, and no additional sample processing, membrane arrays, gels, capillaries, or analytical tools are necessary. Other PCR instrumentation, as known in the art, may be used in the practice of the present invention.

SUMMARY OF THE INVENTION

The present invention is directed to a nucleic acid quantification kit and method for determining the initial concentration or mass fraction of a target nucleic acid present in a sample. More particularly, the present invention relates to the use of real-time competitive quantitative polymerase chain reaction (PCR) and fluorescently labeled oligonucleotide probes to monitor the PCR reaction in real time to determine the copy number of a target nucleic acid sequence in a sample. The method of determining the copy number of a target nucleic acid present in a biological sample comprises the steps of combining in a single reaction vessel at least a portion of the biological sample, a thermostable polymerase, a known amount of a competitor nucleic acid sequence, a pair of oligonucleotide PCR primers, one or more oligonucleotide probes, initiating the PCR reaction, and conducting real time monitoring of the reaction and/or melting curve analysis.

In an illustrated embodiment, the competitor nucleic acid sequence is prepared to have the identical sequence as the target nucleic acid sequence with the exception of a unique section located at an internal position on the competitive nucleic acid sequence. The unique section has the same overall nucleotide composition as the corresponding region of the target nucleic acid sequence but having a substantially different sequence from the corresponding region of the target nucleic acid sequence. The term substantially different is used herein to mean that a probe complementary to the unique region of the competitor will not cross-hybridize to the corresponding region of the target nucleic acid sequence above background levels under the reaction conditions used to conduct the PCR reaction. In one embodiment, the unique region has a randomized sequence relative to the corresponding region of the target nucleic acid sequence.

In another embodiment, the unique section of the competitor nucleic acid sequence differs from the target nucleic acid sequence by only one base pair, similar to a point mutation. In still another embodiment, the unique section of the competitor nucleic acid sequence may be quite a bit different from the corresponding region of the target, varying in length and/or composition, but the competitor and target nucleic acid sequences are amplified with essentially the same efficiency. Such amplification efficiencies can be determined based on CG content and routine experimentation.

The anchor probe is configured to hybridize adjacent to the unique region of the competitor nucleic acid sequence and adjacent to the region of the target nucleic acid sequence corresponding to the unique region of the competitor nucleic acid sequence. The competitor probe is configured to hybridize to the unique region of the competitor nucleic acid sequence, and the target probe is configured to hybridize to the region of the target nucleic acid sequence corresponding to the unique region of the competitor nucleic acid sequence. Accordingly, when the anchor, target and competitor probes hybridize to their respective complementary target nucleic acid sequences and competitor nucleic acid sequences, the donor fluorophore and the first acceptor fluorophore as well as the donor fluorophore and the second acceptor fluorophore are placed in a resonance energy transfer relationship. Therefore, the measurement of fluorescence from the acceptor fluorophore can be used to determine the relative concentrations of the target nucleic acid sequence and the competitor nucleic acid sequence. In illustrated embodiments, the first fluorophore and the second fluorophore both accept energy transfer from the fluorophore donor, but the two acceptor fluorophores emit fluorescent energy at different wavelengths. Thus, the concentrations of the target nucleic acid sequence and the competitor nucleic acid sequence can be measured at the same time.

In still another embodiment, a single-labeled oligonucleotide is used and the desired information is obtained through melting curve analysis.

Another aspect of this invention is a method of quantifying the initial target nucleic acid sequence concentration based on the cycle shift between competitor and target. Provided that the efficiency of amplification is essentially equal for target and competitor, $\log C_o = \log E(\Delta n) + \log T_o$, where $C_o$ is the initial amount of competitor, E is the average efficiency, $\Delta n$ is the cycle shift between target and competitor, and $T_o$ is the initial amount of target. Because this equation has the form $y = mx + b$, a plot of the initial competitor concentration versus the cycle shift between competitor and target will yield a line with the slope equal to the log of the efficiency and a y-intercept equal to the log of the initial target concentration. Since the competitor may be provided in a variety of known initial concentrations, the initial concentration of the target may be determined with relative ease.

One particularly useful application for DNA quantification may be in determining the genomic equivalents of particular viruses in any given clinical sample. Several viruses exhibit their pathological effects at various stages of their replication cycle, and the amount of virus in host cells can serve as an indicator of infection progression and prognosis.

In yet another aspect of this invention is method of determining mass fractions of first and second target nucleic acids present in a test sample, said method comprising the steps of contacting the target nucleic acids with a fluorescent nucleic acid indicator, the indicator being configured to provide a signal related to the quantity of indicator hybridized to the target nucleic acid, the indicator further configured to discriminate the target nucleic acids based on melting temperature, illuminating the test sample, monitoring fluorescent change to generate a melting curve, and using a thermodynamically based signal processing algorithm to determine the mass fraction of the target nucleic acids. The internal standard may consist of an artificial competitor or an endogenous allele that is different from the target nucleic acid sequence by one or more bases. If a known amount of the internal standard is added to the sample, then the initial copy number of the target nucleic acid sequence can be calculated from the mass fraction or ratio against the known amount of internal standard. Particularly useful applications for this type of quantification may be in determining allele frequencies in pooled population samples, monitoring differential allele expression in various cell and tissue types, monitoring gene amplification, or deletion, using imbalance of copy number against the copy number of a pseudogene, and assessing the ratio between different cell types in a mixed tissue sample, such as in margin dissected tissue samples from cancer patients.

Additional features of the present invention will become apparent to those skilled in the art upon consideration of the following detailed description of illustrated embodiments exemplifying the best mode of carrying out the invention as presently perceived.

BRIEF DESCRIPTION OF THE DRAWINGS

FIGS. 2a-b represent detection of amplified products by double strand specific dyes. FIGS. 2c-d represent the Taq Man strategy wherein synthesis of the amplified product results in donor emission. FIGS. 2e-f represent the hybridization probe method wherein two separately labeled probes hybridize to adjacent regions of a nucleic acid sequence resulting in fluorescent resonance energy transfer;

FIG. 3a is a plot of the log fluorescence ratio vs. cycle number. FIG. 3b is a plot of the log copy number vs. the second derivative maximum;

FIGS. 5a-c: represent melting analysis of several nucleic acids. FIG. 5a shows melting peaks generated from a melting curve. The area under each curve is calculated using non-linear regression to fit the melting peak data to a Gaussian curve. FIG. 5b shows various amplification curves on a log fluorescence vs. cycle number plot. FIG. 5c shows the data from FIG. 5b converted into a $\log C_0 = \log E(\Delta n) + \log T_0$ curve (solid line show crossing points from the data of FIG. 5b and dashed line is linear regression);

FIGS. 16a and c show melting data (fluorescence vs temperature) and FIGS. 16b and d show the melting peak data (negative first derivative –dF/dT).

FIGS. 17a and c show melting data (fluorescence vs temperature) and FIGS. 17b and d show the melting peak data (negative first derivative –dF/dT).

DETAILED DESCRIPTION OF THE INVENTION

The present invention allows the quantification of analytes, including analytes that are too low in concentration to be quantitated using standard techniques. The method uses a competitive PCR reaction with real time monitoring during amplification or melting curve analysis, and the presence of an internal standard as a means of calculating the initial concentration of the target sequence. To date, all real-time PCR quantification applications have been limited to quantification relative to an external standard curve. While this technique is very useful, it lacks control for tube-to-tube differences in PCR efficiency. This limitation of quantification with external standards has been addressed by competitive quantitative PCR methods. In these techniques a competitor, with the same primer sites as the target but differing in internal sequence, is spiked at a known concentration into an unknown sample. However, no real-time version of this method is available.

The present disclosure is directed to the use of real-time methods to differentiate target from competitor and thus allow for gene quantification by reference to an internal standard. The methods provide investigators with the advantages of a homogenous, real-time PCR system while giving the added control that internal standards provide.

In accordance with one embodiment, a method is described for conducting real-time competitive quantitative PCR using a competitor with a unique hybridization probe binding site. The competitor will be distinguished from the target by using differently colored hybridization probes for the target and the competitor.

In another embodiment, a method is described for conducting real-time competitive quantitative PCR using a competitor differing from the target by only a single base. The target and the competitor will be distinguished from one another by the differential melting of fluorescently labeled hybridization probes.

Figure 1:
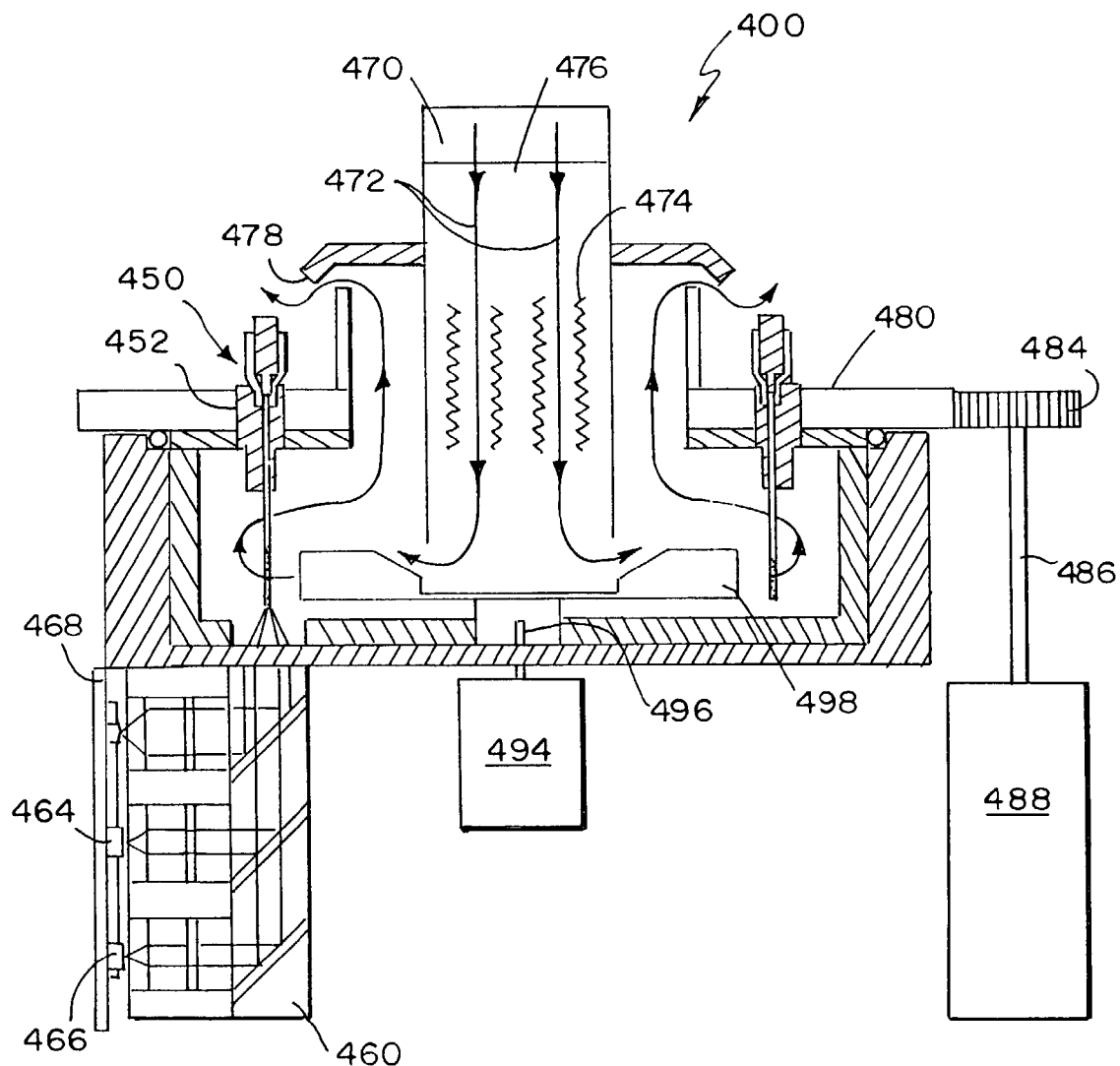
FIG. 1: is a diagrammatic representation of the mechanical and optical design of the LIGHTCYCLER®.

FIG. 1 provides a schematic representation of an embodiment 400 of the LIGHTCYCLER®, a thermal cycler that may be used in accordance with the described methods. As shown in FIG. 1, air is taken in through an aperture 470 and generally follows the flow path indicated by the lines 472. The temperature of the air, and thus the temperature of the sample container 450, is controlled with heating cartridge 474, which is positioned within a central duct 476, and fan 498, which is provided to move the air in the indicated path 472. The fan is driven via a shaft 496 and a motor 494. The fan 498 forces air into the aperture 470 and out via exhaust ports 478. In the illustrated embodiment, twenty-four sample containers 450 (two of which are represented in FIG. 1) are symmetrically arranged around the heating cartridge 474 and the central duct 476. The sample containers 450 are received by sleeves 452 in a circular carousel 480. The carousel 480 is positioned by a stepper motor 488 provided with a drive gear 484 that is connected to the motor 488 via a shaft 486. Fluorescence from each sample container is obtained by photo array 460, which includes an excitation radiation source 468 and photodetectors 464 and 466. More details of the LIGHTCYCLER® may be found in U.S. patent application Ser. No. 08/869,275, herein incorporated by reference. It is understood that this described embodiment is merely exemplary and that other thermal cyclers may be used within the scope of the invention.

By way of illustration, amplifying an analyte by PCR comprises the steps of placing a biological sample comprising the target nucleic acid sequence in a capillary vessel, raising the temperature of the biological sample from a first temperature ("annealing temperature") to a second temperature ("denaturation temperature") wherein the second temperature is higher than the first temperature, illustratively at least 15° C. higher than the first temperature, holding the biological sample at the second temperature for a predetermined amount of time, lowering the temperature of the biological sample from the second temperature to at least as low as the first temperature and holding the biological sample at a temperature at least as low as the first temperature for a pre-determined length of time. The temperature of the biological sample is then raised back to the second temperature, and the biological sample is thermocycled a predetermined number of times.

In one embodiment, the method of amplifying a DNA sequence comprises a two temperature profile wherein the samples are cycled through a denaturation temperature and an annealing temperature for a predetermined number of repetitions. Other PCR profiles may be used within the scope of this invention. For example, the PCR reaction can also be conducted using a three temperature profile wherein the samples are cycled through a denaturation temperature, an annealing temperature, and an elongation temperature for a predetermined number of repetitions.

Figure 2A:
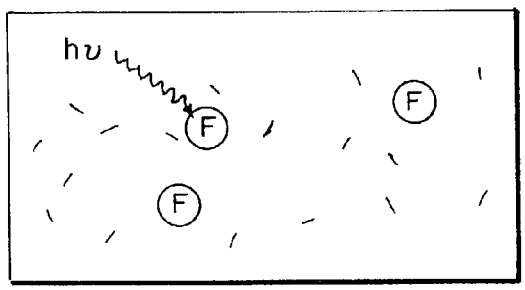
FIGS. 2a-f: are diagrammatic representations of the various fluorescent-based methods of detecting amplification products.

In illustrated embodiments, the PCR reaction is conducted in the presence of fluorescent entity to allow real-time monitoring of the reaction. Several detection formats based on target dependent fluorescent signaling have been disclosed which enable continuous monitoring of the generation of amplification products. See, for example, Wittwer et al., "Continuous Fluorescence Monitoring of Rapid Cycle DNA Amplification," BioTechniques, Vol. 22, No. 1, 130-138, 1997), hereby incorporated by reference. These detection formats include but are not limited to:

1. Use of fluorescent double-stranded DNA recognizing compounds (see FIGS. 2a-b)

Figure 2B:
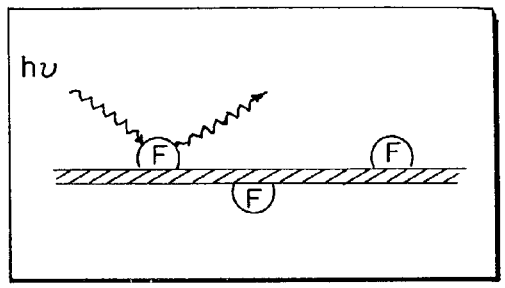

Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double- stranded DNA (FIG. 2b). Preferably, only dyes such as SYBR™ Green I, which do not affect the efficiency of the PCR reaction are used.

Figure 2C:
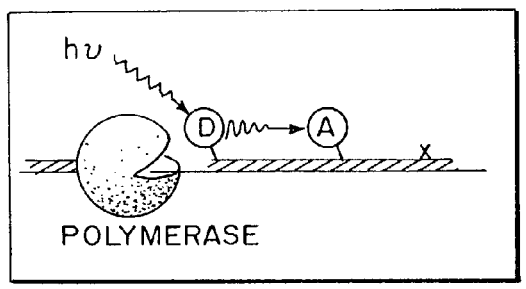

2. Tag Man principle (see FIGS. 2c-d)

Figure 2D:
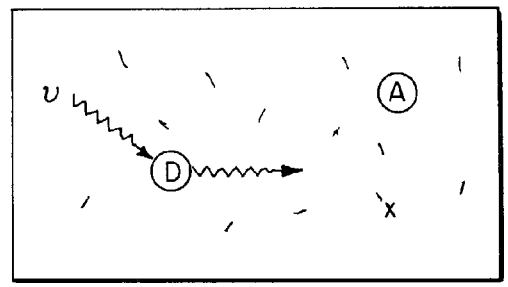

In order to detect the amplification product, a single-stranded hybridization probe is used. The hybridization probe is labeled with a fluorescent entity, the fluorescence emission of which is quenched by a second label on the same probe that acts as a quenching compound. During the annealing step of the PCR reaction, the probe hybridizes to its target sequence (FIG. 2c), and, subsequently, during the extension of the primer, a DNA polymerase having a 5'-3'-exonuclease activity digests the hybridization probe into smaller pieces, separating the fluorescent entity from the quencher compound (FIG. 2d). After appropriate excitation, fluorescence emission can be monitored as an indicator of accumulating amplification product.

3. Molecular beacons

Similar to the Taq Man Probes, a molecular beacon oligonucleotide is labeled with a fluorescent compound and a quencher compound, which due to the secondary structure of the molecule are in close vicinity to each other. Upon binding to the target DNA, the intramolecular hydrogen bonding is broken, and the fluorescent compound located at one end of the probe is separated from the quencher compound, which is located at the opposite end of the probe. See, for example, U.S. Pat. No. 5,118,801, hereby incorporated by reference.

4. Increased FRET upon hybridization (see FIGS. 2e-f)

For this detection format, two oligonucleotide hybridization probes, each labeled with a fluorescent moiety, are used which are capable of hybridizing to adjacent but non-overlapping regions of one strand of the amplification product. Preferably, one oligonucleotide is labeled at the 5' end and the second oligonucleotide is labeled at the 3' end. When hybridized to the target DNA, the two fluorescent labels are brought into close contact, such that fluorescence resonance energy transfer (FRET) between the two fluorescent moieties can take place (FIG. 2f). As a consequence, the hybridization can be monitored through excitation of the donor moiety and subsequent measurement of fluorescence emission of the second acceptor moiety.

In a similar embodiment, only one fluorescently labeled probe is used, which together with one appropriately labeled primer may also serve as a specific FRET pair. See Bernard et al., "Integrated Amplification and Detection of the C677T Point Mutation in the Methylenetetrahydrofolate Reductase Gene by Fluorescence Resonance Energy Transfer and Probe Melting Curves," Anal. Biochem. 255, p. 101-107 (1998), hereby incorporated by reference.

Usually, the hybridization probes as disclosed have sequences completely identical with or exactly complementary to the sequence of the analyte. However, it is also within the scope of the invention for probes to contain one or several mismatches, as long as the probes are capable of hybridizing to the analyte under appropriate hybridization conditions. In any case, it has been proven to be particularly advantageous if the sequence identity or complementarity is 100% over a range of at least 10 contiguous residues. It has also been proven to be advantageous if the length of the probe does not exceed 100 nucleotides, preferably not more than 40 nucleotides.

Fluorescence resonance energy transfer occurs between two fluorophores when they are in physical proximity to one another and the emission spectrum of one fluorophore overlaps the excitation spectrum of the other. The rate of resonance energy transfer is $(8.785E^{-5}) (t^{-1}) (k^2) (n^{-4}) (q_D) (R^{-6}) (J_{DA})$, where:

t=excited state lifetime of the donor in the absence of the acceptor;

$k^2$=an orientation factor between the donor and acceptor;

n=refractive index of the visible light in the intervening medium;

$q_D$=quantum efficiency of the donor in the absence of the acceptor;

R=distance between the donor and acceptor measured in Angstroms; and $J_{DA}$=the integral of $(F_D)$ $(e_A)$ $(W^4)$ with respect to W at all overlapping wavelengths with:

$F_D$=peak normalized fluorescence spectrum of the donor;

$e_A$=molar absorption coefficient of the acceptor $(M^{-1} cm^{-1})$; and $W^4$=wavelength (nm).

For any given donor and acceptor, a distance where 50% resonance energy transfer occurs can be calculated and is abbreviated $R_0$. Because the rate of resonance energy transfer depends on the 6th power of the distance between donor and acceptor, resonance energy transfer changes rapidly as R varies from $R_0$. At 2 $R_0$, very little resonance energy transfer occurs, and at 0.5 $R_0$, the efficiency of transfer is nearly complete, unless other forms of de-excitation predominate.

The fluorescently labeled oligonucleotides are designed to hybridize to the same strand of a DNA sequence such that the donor and acceptor fluorophores are separated by a distance ranging from about 0 to about 25 nucleotides, more preferably about 0-5 nucleotides, and most preferably about 0-2 nucleotides. A particularly preferred spacing between the donor and acceptor fluorophores is about 1 nucleotide.

When one of the labeled oligonucleotides also functions as a PCR primer ("probe-primer"), then the two fluorescent entities are on opposite strands of a DNA sequence. In this embodiment, the donor and acceptor fluorophores are preferably within about 0-15 nucleotides and more preferably within about 4-6 nucleotides.

Unless both of the fluorescently labeled oligonucleotides are hybridized to their complementary sequence on the targeted DNA, the distance between the donor fluorophore and the acceptor fluorophore generally is too great for resonance energy transfer to occur. Thus, in the absence of hybridization, the acceptor fluorophore and the donor fluorophore are not in resonance energy transfer relationship and excitation of the donor fluorophore will not produce a detectable increased fluorescence by the acceptor fluorophore.

Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LCRed 640 or fluorescein/LCRed 705. LCRed 640 and LCRed 705 have been previously described in published European Application EP 0 567 622, the disclosure of which is expressly incorporated herein.

The thermal stability of a DNA duplex relies on duplex length, GC content, and Watson-Crick base pairing. Changes from Watson-Crick base pairing destabilize a duplex by varying degrees depending on the length of the mismatched duplex, the particular mismatch, the position of the mismatch, and neighboring base pairs. Accordingly, the percent identity of the hybridization probes to their target complementary sequence directly affects the temperature at which the hybridization probe will separate (melt) from the complementary strand. The greater the difference between the probe and the target complementary sequence, the lower the temperature needed to separate the hybridizing strands.

5. Single-Labeled Oligonucleotides

Single-labeled oligonucleotides are oligonucleotides having a singular fluorescent label. The single-labeled oligonucleotides may be used independently of any other fluorescent entities, and fluorescent change occurs due to the sequence of the bases located on the complementary strand. See U.S. patent application Ser. No. 09/927,842, filed Aug. 10, 2001, hereby incorporated by reference. Depending on various factors, such as the fluorescent entity used and the sequence of the complementary strand, hybridization may result in either a decrease or increase in fluorescence.

Probe Systems for the LIGHTCYCLER®

Figure 2E:
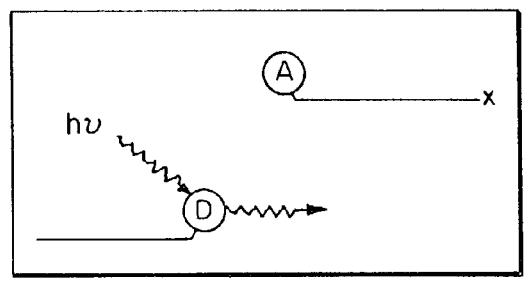
Figure 2F:
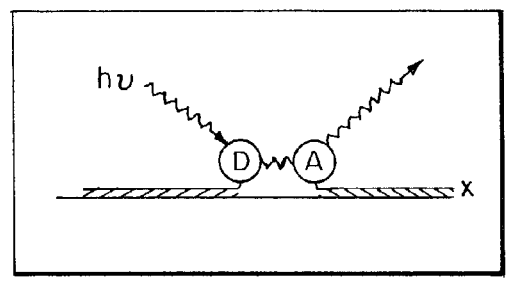

A sequence specific probe system for the LIGHTCYCLER® has been developed for use in the present invention wherein two fluorophores of a FRET pair are brought close together by hybridization during PCR so that resonance energy transfer occurs (see FIGS. 2e-f). Two adjacent hybridization probes are designed to hybridize between the PCR primers, one labeled at the 3' end with a donor fluorophore, the other labeled at the 5' end with an acceptor fluorophores. As product accumulates during PCR, the probes hybridize next to each other during the annealing segment of each cycle. Fluorescence energy transfer to the acceptor dye increases with hybridization and is plotted as a ratio of acceptor to donor fluorescence. For quantification, the fluorescence preferably is monitored once each cycle near the end of a two-temperature annealing extension segment. A version of the LIGHTCYCLER® has been optimized for use with one donor dye, fluorescein, and two different acceptor dyes, LIGHTCYCLER® Red 640 (LCRed 640) and LIGHTCYCLER® Red 705 (LCRed 705). While FRET oligonucleotide pairs are commonly used with the LIGHTCYCLER® and are used various examples herein, it is understood that other sequence specific probes may be used within the scope of this invention.

Real-Time Kinetic PCR on the LIGHTCYCLER®

Figure 3A:
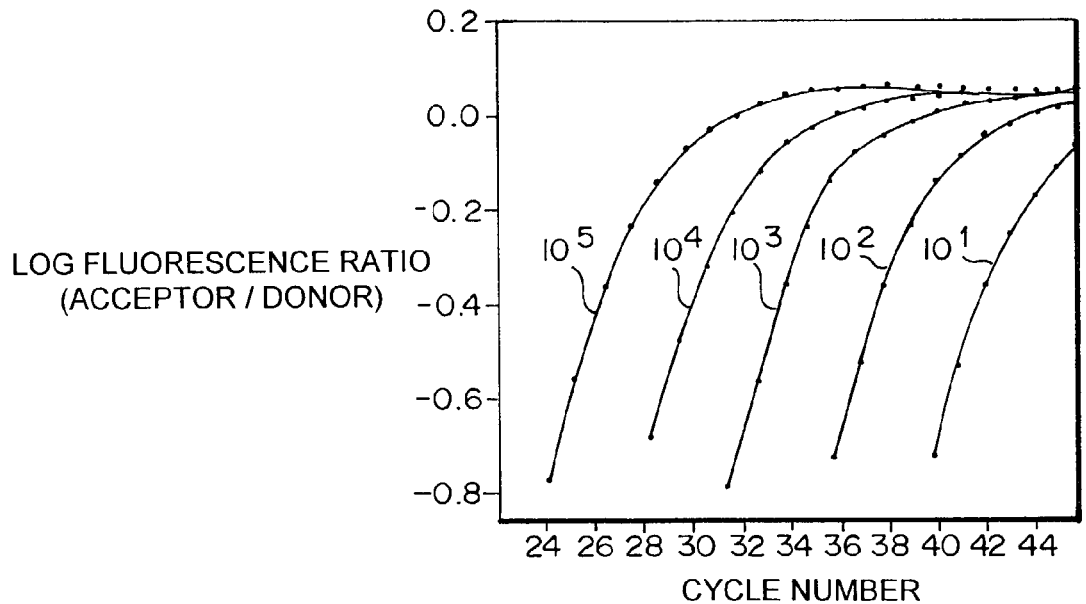
FIGS. 3a-b: represent typical external standard curves using hybridization data.
Figure 3B:
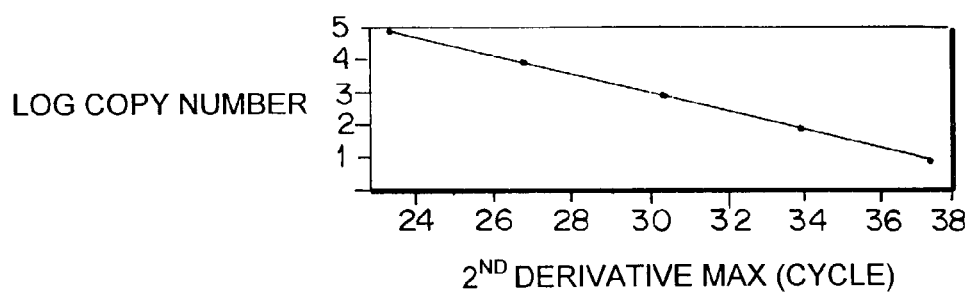

The LIGHTCYCLER® can be used with either double stranded DNA binding dyes such as SYBR™ Green I or hybridization probes to monitor the PCR reaction. FIGS. 3a and 3b show typical external standard curves using hybridization probes. The donor probe was labeled with fluorescein and the acceptor with LCRed 640. The data are plotted as the ratio of acceptor to donor fluorescence. The initial concentration of standard ranged from $10^5$ to $10^1$ copies of target per 10 ÿl reaction.

Mutation Detection using the LIGHTCYCLER®

Monitoring once each cycle provides useful information for quantification. Additional information is available if fluorescence is monitored continuously during temperature transitions. The hybridization state of the probes can be determined by measuring the change in fluorescence as the temperature is varied. Hybridization probe melting occurs at a characteristic temperature that can be exploited for product identification and mutation detection.

Quantification by Kinetic PCR

Figure 4A:
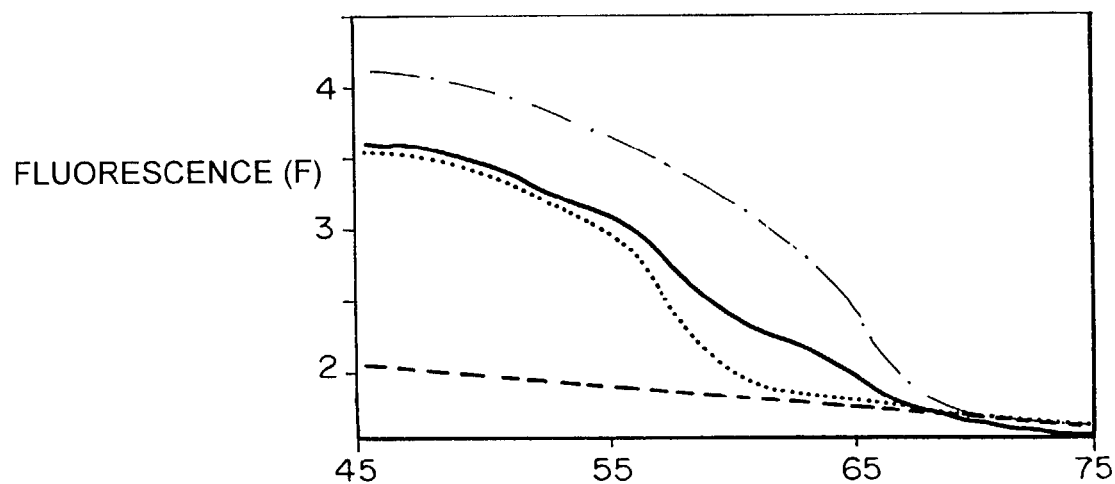
FIGS. 4a-b: represent a typical standard curve generated by plotting fluorescence vs. temperature (FIG. 4a) and the derivative of that curve plotted against temperature (FIG. 4b), with homozygous mutant (. . . ), homozygous wild type (-•-), heterozygous mutant (-), and no DNA (--)
Figure 4B:
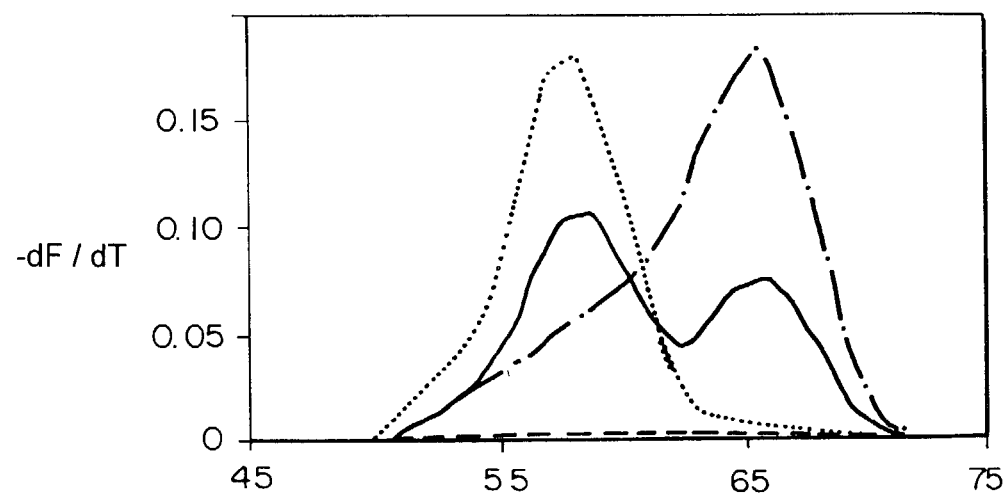

The temperature dependence of the fluorescence from hybridization of the probes may be demonstrated with fluorescence vs. temperature plots (FIG. 4a). The illustrated plots were generated by monitoring a single sample every 0.1° C. during a slow (0.2° C./second) temperature ramp from 45° C. to 75° C. The product is denatured and then rapidly cooled (10° C./second) to 45° C. At low temperature the probes hybridize to single-stranded product and the fluorescence ratio (for example LCRed 640/ fluorescein) increases. During heating, the probes dissociate in the 55 to 65° C. range, returning the fluorescence ratio to background levels. The derivative of this curve is calculated with respect to temperature and plotted against temperature (FIG. 4b). This produces a melting peak centered around the $T_m$ of the probe. Discrimination based on hybridization temperatures is a powerful tool for mutation detection.

A Method Combining Mutation Detection with Quantification

The use of an internal standard in competitive quantitative PCR assays involves careful selection of the competitor used as the internal standard. The competitor and the target in competitive quantitative PCR assays must fulfill contradictory criteria. The two nucleic acid sequences must amplify with the same efficiency, generally requiring them to be as similar as possible. But they must also be differentiable and not prone to heteroduplex formation, requiring them to be dissimilar.

The ultimate in similarity between target and template is a single base pair change. It is extremely unlikely that a single base change would have a significant effect on efficiency of amplification. In accordance with one embodiment of this invention, the LIGHTCYCLER® is used to differentiate between a target and a competitor differing by only a single base pair, as in a single base pair mutation. Under proper conditions, hybridization probes detect only one of the DNA strands, so heteroduplex formation during amplification does not affect the results.

Figure 5A:
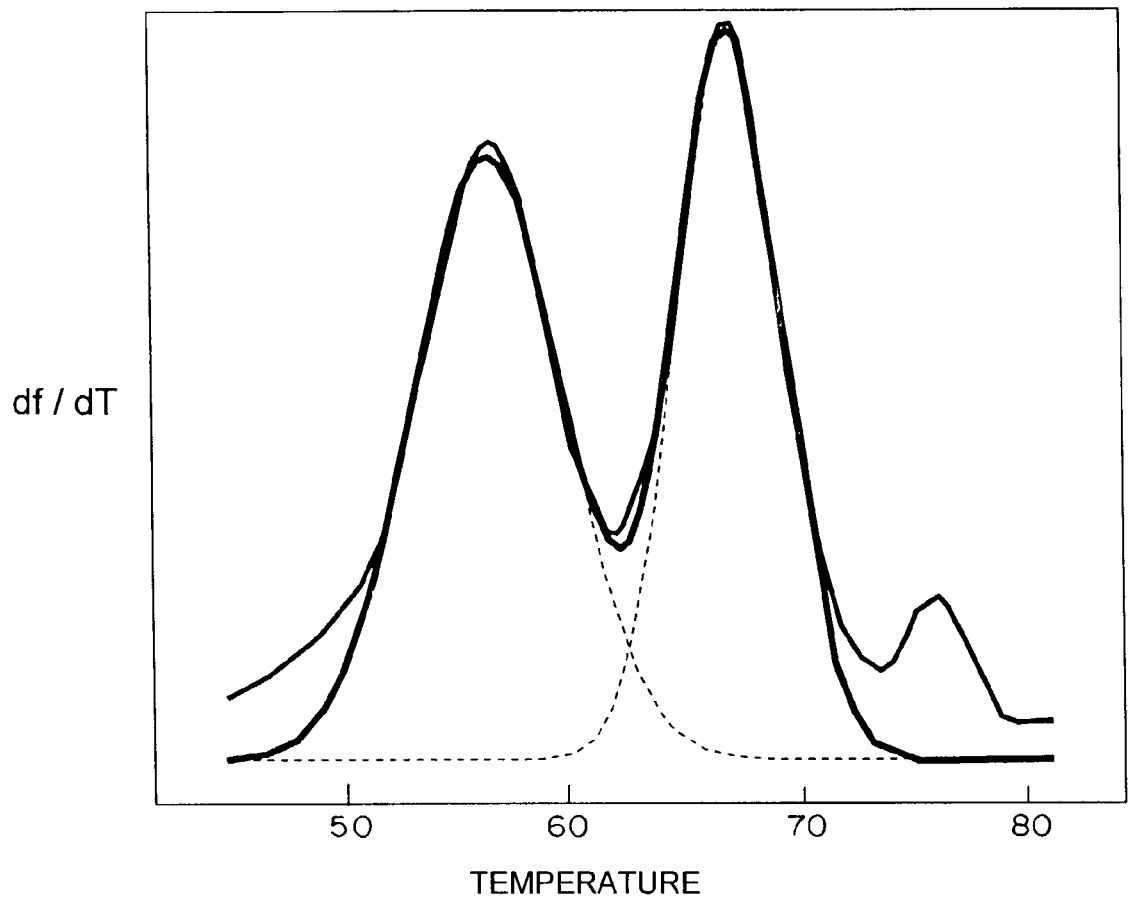

In the course of the development of the LIGHTCYCLER® software has been developed for analysis of real-time fluorescence data. FIG. 5a is a representative melting curve. The software calculates the area under each curve using non-linear regression to fit the melting peak data to a Gaussian curve. This module serves as the basis of the software for quantification using the $T_m$ method. The relative peak areas of target and competitor are used to calculate the relative amounts of the two products.

FIG. 5b shows various amplification curves on a log fluorescence vs. cycle number plot. For each curve, the point in the amplification curve where the second derivative is at a maximum is identified, that is, the point of maximal increase in the rate of increase. This fractional cycle number is used to describe the position of the amplification curve. Unlike traditional "threshold" methods that define the curve position relative to background noise, this approach allows the automatic determination of the positions of the amplification curves based on the shape of the curve. See U.S. Pat. No. 6,387,621, herein incorporated by reference. This module serves as the basis of the software for the multi-color method. The relative amounts of target and competitor are determined by looking at the fractional cycle difference in the positions of the two amplification curves, as shown in FIG. 5c.

A Method Combining Kinetic PCR with Internal Standards

In an alternative embodiment, the competitor/internal standard is distinguished from the target nucleic acid by differential probe hybridization during the PCR reaction. Thus, the reaction is monitored and hybridization is detected as it occurs: a "real-time probe capture." This makes it possible to determine the amount of the target and competitor kinetically, not merely from an endpoint measurement.

In an illustrated embodiment, a kinetic internal standard quantification method is used where the target and competitor differ only at the probe binding site. The competitor probe and the target probes are labeled with differently colored fluorophores (LCRed 640 and LCRed 705). Both of these probes are paired with a longer fluorescein "anchor probe." Both target and competitor are monitored simultaneously, once-each-cycle. Illustratively, the optical design of the system used in this embodiment is three color and based on paraxial epifluorescent illumination of the capillary tip. Total internal reflection along the capillary axis increases signal strength by about 10-fold. The excitation source is a "super bright" blue light emitting diode. Fluorescence signals are acquired from photodiodes after bandpass filtering in the three channels at 520 nm, 640 nm and 705 nm.

Like the $T_m$ method, heteroduplex formation is not a concern, as only one of the DNA strands is detected by the hybridization probes. Work with external standards has shown that the position of amplification curves is more reproducible than the final fluorescence levels. Accordingly, since data are collected every cycle in this kinetic method, the more reliable data from earlier cycles are used. Advantageously, the present method does not depend on a single measurement to define the product ratios. Instead, the relative positions of the entire amplification curves are used to determine the ratio of the two products.

If reactions containing the same target and competitor concentrations give amplification curves that are in the same position, then the shift in the curve position between target and competitor can be used to calculate the ratio of target and competitor. This method provides precise estimates of target and competitor amounts.

Delta C. T Equation Determination

The above approach has not previously been used with quantification with internal standards. Thus, a convenient, preferably linear mathematical relationship between the target and the competitor's curve positions and their relative concentrations is needed. If target and competitor have the same efficiency, then at the second derivative maximum for the target:

$$T_{nt}=T_o(E)^{nt}$$

where $T_{nt}$ is the amount of target at the second derivative maximum, $T_o$ is the initial amount of target, E is the average efficiency of the reaction, and nt is the fractional cycle number of the second derivative maximum. Similarly at the second derivative maximum for the competitor:

$$C_{nc}=C_o(E)^{nc}$$

where $C_{nc}$ is the amount of competitor at the second derivative maximum, $C_o$ is the initial amount of competitor, E is the average efficiency of the reaction, and nc is the fractional cycle number of the second derivative maximum.

The second derivative method is sensitive to the shape of the amplification curve, not the absolute fluorescence level. The position of the amplification curve should not be significantly affected by differences in signaling efficiency between LCRed 640 and LCRed 740. The point where the second derivative is at a maximum does not reflect a certain signal level but rather the accumulation of a certain amount of product. At their respective second derivative maxima, the concentrations of target and competitor should be equal. Therefore:

$$C_{nt}=T_{nc}$$

And so it follows that:

$$C_o(E)^{nc}=T_o(E)^{nt}$$

Rearranging:

$$C_o/T_o=(E)^{nt}/(E)^{nc}$$

Taking the log of both sides:

$$\log(C_o/T_o)=\log[(E)^{nt}/(E)^{nc}]$$

$$\log C_o - \log T_o = nt\log E - nc\log E$$

$$\log C_o - \log T_o = \log E(nt-nc)$$

nt-nc is the cycle shift between target and competitor which we can call $\Delta n$, substituting:

$$\log C_o - \log T_o = \log E(\Delta n)$$

And rearranging:

$$\log C_o = \log E(\Delta n) + \log T_o$$

This delta C.T. equation has the form y=mx+b, so a plot of the initial competitor concentration versus the cycle shift between competitor and target will give a line with the slope equal to the efficiency and a y-intercept equal to the log of the initial target concentration.

EXAMPLE 1

The following experiment is conducted to confirm that equal concentrations of initial target and competitor template give equal second derivative maxima.

Equal concentrations of purified target and competitor PCR are mixed together at concentrations ranging from 10 to $10^6$ copies per reaction in 10 fold steps and amplified for 35 cycles. The positions of the second derivative maximum for all of the target and competitor pairs are compared and it is expected that the second derivative maxima are the same for equal concentrations. This experiment is repeated five times and statistical tests are conducted to determine if a zero difference in crossing point is within the 95% confidence interval of $\Delta n$. If the difference is not zero, but the difference is consistent, a "$\Delta\Delta n$" can be used, that is, the difference in curve position less any systematic difference between the two channels.

EXAMPLE 2

The following experiment is conducted to confirm that the dynamic range of the assay is at least an order of magnitude on either side of the target concentration.

If either the target or the competitor is present in great excess, the more concentrated product will reach a plateau before the less concentrated product rises above the detection limit of the instrument. The LIGHTCYCLER® has a detection range of approximately two orders of magnitude. This detection range defines the upper limit of the dynamic range. A minimum dynamic range of at least a one order of magnitude difference is desirable.

The maximum difference in target/competitor ratio that still allows both products to be detected is tested. Target at $10^4$ copies per reaction is mixed with competitor ranging from $10^2$ to $10^6$ copies per reaction in one third log steps. A dynamic range of between one and two orders of magnitude is expected. The target copy number is calculated using the kinetic method and is compared to the actual target concentration. This experiment is repeated five times and the precision of the calculated target number is determined.

Once the maximum target to competitor difference has been established with $10^4$ copies of target, the maximum difference in target/competitor ratio across a range of target concentrations is determined. Target from $10^1$ to $10^6$ copies per reaction is mixed with competitor differing by 2-fold, 5-fold, 10-fold, 20-fold up to the maximum difference in target/competitor ratio defined by the experiments above. The target copy number is calculated using the kinetic method and is compared to the actual target concentration. This experiment is repeated five times and the precision of the calculated target number is determined.

EXAMPLE 3

The following experiment is conducted to determine the effect of target copy number on the accuracy and precision of the assay.

Results of the PCR experiments are analyzed for precision and accuracy. For each starting copy number of target from $10^1$ to $10^6$, a 95% confidence interval is calculated. The inter-assay and intra-assay precision is also calculated by measuring the coefficient of variation (% CV) within and across experiments for each starring copy number of target from $10^1$ to $10^6$. At $10^1$ or $10^2$ copies, it is expected that the % CVs will be around 100%. At the higher copy numbers the % CVs are expected to be around 25%. A 25% CV would allow easy discrimination of two-fold differences.

Software

The curve positions are calculated using the second derivative maximum method. This method, which depends on curve shape and not absolute signal, is believed to be more resistant to differences in signaling efficiency between the channels. The cycle shift is plotted against the initial competitor concentration and a line is fit to the data. If the single point method gives reasonable answers (% CV <50), then the software supports this calculation as well.

EXAMPLE 4

A method for real-time competitive quantitative PCR in the LIGHTCYCLER® using a competitor which differs from the target by only a single base is described in the following experiment. The target and the competitor are distinguished by the differential melting of fluorescently labeled hybridization probes.

Experimental Design

Figure 7:
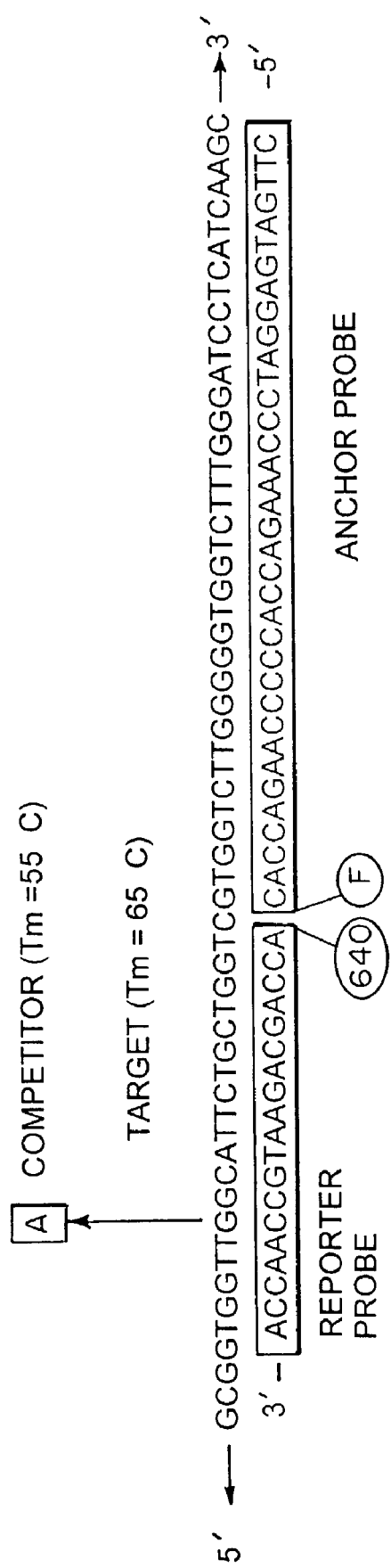
FIG. 7: represents the nucleotide sequences of the HER-2/neu (target) (SEQ ID NO. 15), its competitor (SEQ ID NO. 16), the reporter (SEQ ID NO. 17) and anchor probes (SEQ ID NO. 18); the predicted melting temperatures Tm of the reporter probe hybridized to either the target or competitor are shown.

The target for quantification in this example is the human HER-2/neu gene. The HER-2/neu gene is amplified in 25% of breast tumors and the degree of amplification (usually 2-50 fold) correlates with survival time. FIG. 7 shows a design of probes for HER-2/neu. With this design, the competitor has a CA mismatch with the hybridization probe. A CA mismatch in the center of a probe results in a $T_m$ shift of 5-10° C., sufficient to allow for separation of the matched and mismatched melting peaks. The primers that flank these probes (not shown) were designed using the Primer Designer™ software (Scientific and Educational Software).

Construction of the Competitor

Wild type HER-2/neu PCR product generated from human genomic DNA is used as the target. The competitor is generated by amplification of HER-2/neu from genomic DNA with a mutagenic PCR primer containing a G to A change, as shown in FIG. 7. The PCR products are gel purified, diluted, and then reamplified with the amplification primers. These products are gel purified and used as target and competitor. The introduction of the mutation is confirmed by sequencing.

Target and competitor concentrations are determined by Molecular Probes PicoGreen dsDNA quantification assay or by the limiting dilution method as discussed above.

Probe Synthesis and Purification

The probes are shown in FIG. 7. The anchor probe is 3' fluorescein labeled. The acceptor probe is labeled on the 5' end with LIGHTCYCLER® Red 640 and is blocked on the 3' end by a phosphate. Probes are synthesized and purified as discussed above.

Quantification with Internal Standards

First, a determination is made that the signals from target and competitor (that is, the melting peak areas) are proportional to the amount of target present. This is first done with purified PCR products. Wild type and competitor HER-2/neu are mixed in equal concentrations from $10^{10}$ to $10^{12}$ copies per tube. The melting peaks are obtained by rapidly dropping the temperature below the annealing temperature of the probes and then slowly heating (0.2° C./second) to a temperature 15° C. above the melting temperature of the probes. Fluorescence is acquired every 0.1° C. during the ramp. The ratio of the areas under the best-fit Gaussians is compared to the known initial target/competitor ratio of 1.0. Statistical tests produce a ratio of 1.0 that falls within the 95% confidence intervals.

Preferably, not only do equal amounts of purified PCR product produce equal signal; the proportions should stay constant throughout amplification. Accordingly, purified target and competitor PCR products are mixed together at equal concentrations from $10^1$ to $10^6$ copies per reaction in 10-fold steps, amplified for 35 cycles, and then studied by performing a melting curve analysis. This experiment is repeated five times. The ratio of the areas under the best fit Gaussians is compared to the known initial target/competitor ratio of 1.0. Statistical tests are conducted to determine whether a ratio of 1.0 falls within the 95% confidence intervals, and results show that the amplification efficiencies of the target and competitor molecules are indistinguishable.

Figure 14:
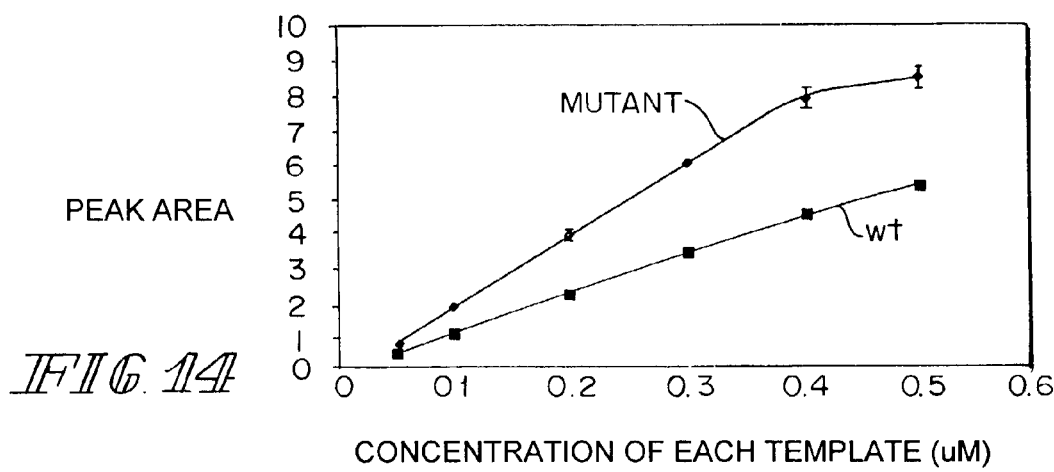
FIG. 14: represents the correlation between melting peak area and product concentration for mutant and wild-type HER-2/neu targets detected by hybridization probes using melting curve analysis software. Artificial oligonucleotide templates were mixed with probes at various concentrations and melting peak-area was determined using LIGHTCYCLER® melting curve analysis software.

The final amount of PCR product produced, and thus available for melting curve analysis, is dependent upon many variables, but will not exceed the amount of primer used. Hybridization probe reactions typically use between 0.1 ÿM and 0.5 ÿM primers, so the highest concentration of product that can theoretically be produced by PCR would be between 0.1 and 0.5 ÿM. Preliminary experiments indicated that accurate measurement of product amounts by melting-peak areas needed probe concentrations in excess of the total amount of PCR product produced after amplification. This posed problems for the standard LIGHTCYCLER® optics, since fluorescein probe concentrations higher than ~0.2 ÿM will exceed the detection level in the F1 channel. To over come this problem the F1 optics of a LIGHTCYCLER® was modified to block ~90% of the fluorescent signal transmitted to the F1 detector. In this manner higher concentrations of probe could be used so that the probe concentrations are always in excess of product. Reconstructed melting experiments using artificial templates of known concentration were designed to measure peak areas with this modified instrument using excess probe. FIG. 14 shows that there is a linear correlation between melting peak areas and product concentrations between 0.1 and 0.4 ÿM using 1.0 ÿM of each probe. These results indicate that end-point PCR product (using primer concentration of 0.5 ÿM or less) will consistently produce melting peak areas within this linear range and yield quantitative information.

Dynamic range of quantification by melting peak analysis

A linear relationship between melting peak area and amount of PCR product could be established for a ten-fold difference in the relative amounts of the two molecules in reconstructed melting experiments using the conventional LIGHTCYCLER® melting analysis software. To broaden the dynamic range of this technique, a novel method of melting curve analysis was developed based on a Thermodynamic Modeling based Signal Processing (TMBSP, see Example 6) of the melting curve data: the components of a heterogeneous melting curve are quantitatively described in terms of their volume fractions with respect to homogeneous melting curves for each component.

Figure 15:
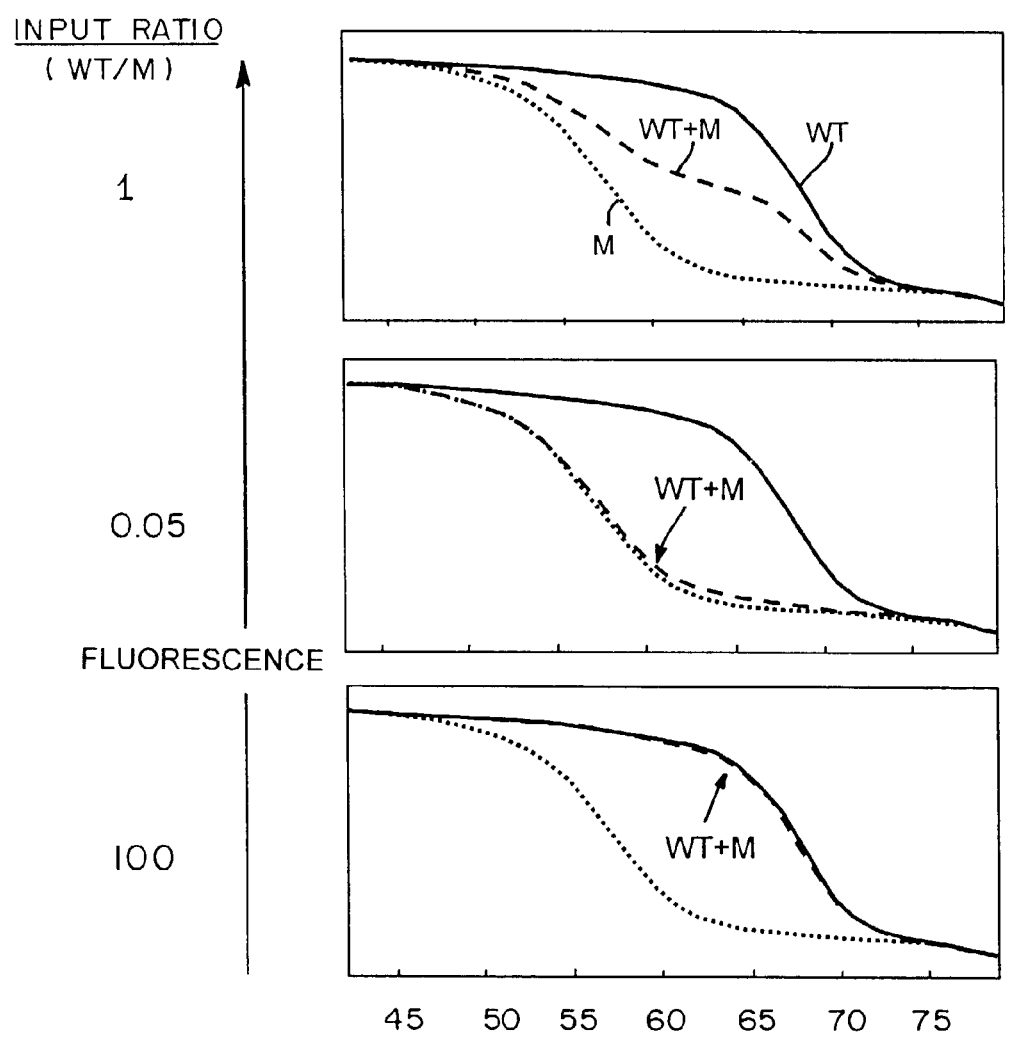
FIG. 15: represents quantification of mutant (M) and wild-type (WT) HER-2/neu targets by melting curve analysis following PCR amplification. Mutant and wild-type templates, both individually and mixed at various ratios (input ratio), were amplified for 40 cycles of PCR and melting curves were generated from the PCR products. Melting curves were analyzed by the TMBSP algorithm to determine the ratios of mutant and wild-type PCR products (output ratio).

FIG. 15 shows the results of mixing wild-type (WT) and mutant (M) template molecules at input ratios ranging from 20:1 to 1:100, followed by 45 cycles of PCR amplification and melting curve analysis to identify the relative amounts of wild-type and mutant product after amplification (output ratios). These results show that TMBSP analysis of melting curves can distinguish 1 molecule in 100 following 45 cycles of PCR amplification.

Precision of the assay

Table 1 summarizes the accuracy of quantification by melting-peak analysis. Ratios of as much as 1 in 50 are discernable with reasonable accuracy and at a 100-fold difference the minor species can still be routinely detected, but with poorer accuracy.

TABLE 1

Ratios of Mutant and Wild-type alleles calculated from melting-curve analysis

| | Amount of input wild-type compared to mutant | | | | | | |
|---|---|---|---|---|---|---|---|
| | equal | 2X | 5X | 10X | 20X | 50X | 100X |
| Mutant Copy number | M/WT Ratio / st dev | M/WT Ratio / st dev | M/WT Ratio / st dev | M/WT Ratio / st dev | M/WT Ratio / st dev | M/WT Ratio / st dev | M/WT Ratio / st dev |
| $10^6$ | 1.040 / 0.041 | | | | | | |
| $10^5$ | 1.030 / 0.069 | 0.544 / 0.044 | 0.230 / 0.008 | 0.108 / 0.007 | 0.052 / 0.008 | | |
| $10^4$ | 1.010 / 0.055 | 0.517 / 0.009 | 0.227 / 0.006 | 0.117 / 0.010 | 0.062 / 0.005 | 0.027 / 0.011 | 0.012 / 0.007 |
| $10^3$ | 0.943 / 0.068 | 0.503 / 0.034 | 0.216 / 0.015 | 0.104 / 0.005 | 0.051 / 0.003 | 0.034 / 0.005 | 0.018 / 0.003 |
| $10^2$ | 0967 / 0.173 | 0.493 / 0.036 | 0.207 / 0.030 | 0.116 / 0.018 | 0.058 / 0.006 | 0.022 / 0.004 | 0.011 / 0.006 |

Because of the exponential nature of PCR, small differences in reaction efficiencies will have ever greater effects with increasing cycle number. However, the fact that quantitative information can be obtained after 45 cycles of amplification indicates that reaction efficiencies of mutant and wild-type molecules in practice do not differ significantly enough to affect product quantification.

Software

Current analysis software used to assess the data takes melting curve data, differentiates with respect to temperature to give melting peaks, and then calculates the best fit of 1 to 3 Gaussian curves to the melting peak data. The only user input is the number of Gaussians to fit. The current software can be further modified to make it possible to analyze melting data for quantification.

The parameters in a Gaussian curve equation are the area of the peak, the position of the center of the peak (mean) and the width of the peak (standard deviation). The preferred currently available software allows all three values to float. For quantification with internal standards, the number of curves is illustratively two, and the means are known to be within the reproducibility of the machine. Only the area and standard deviation of the curve need to float completely free. The non-linear regression software can be modified to allow the user to enter the expected melting temperatures of target and competitor and the concentration of the competitor in each sample.

The relative melting peak areas are used to calculate HER-2/neu target copy number. Users enter the competitor copy number for each sample. The software takes the data from multiple samples and plots the log of the final target/competitor ratio versus the log of the competitor concentration. This plot should give a line a slope of −1 with a y-intercept equal to the log of the initial target concentration.

EXAMPLE 5

The following experiment is conducted to determine quantification of HPV 16 using internal quantification standards with real-time fluorescence PCR on the LIGHTCYCLER®.

DNA/oligonucleotides

Human Papilloma virus DNA is subcloned into pBR322. The following probes and primers are used for cloning, amplification, and detection.

```
16HI13:                                     (SEQ ID NO. 1)
5'-GGGGATCCACTTCAGTATTGC-3';

16RI9:                                      (SEQ ID NO. 2)
5'-GGGAATTCCATGGCTGATCCTGCAGGTAC-3';

16ICS:                                      (SEQ ID NO. 3)
5'-GATCCTGCAGGTACCGATCGGATAGTGAGCGAGAGATAGGTAGGGAT
GGTTTTATGTAG-3';

ICSp913/640:                                (SEQ ID NO. 4)
5'-LC640-CTACCTATCTCTCGCTCACTATCCATC-P-3';

16p913:                                     (SEQ ID NO. 5)
5'-LC705-ATTACATCCCGTACCCTCTTCCCCATT-p-3';

900f16:                                     (SEQ ID NO. 6)
5'-CCATGGCTGATCCTGCAGGTAC-3';

1300r16:                                    (SEQ ID NO. 7)
5'-CCACTTCAGTATTGCCATACCC-3';
```

-continued

```
16an913:                                    (SEQ ID NO. 8)
5'-CTCGTCATCTGATATAGCATCCCCTGTTTTTTTTCCACTACAGCCT
CTACATAAAACC-FITC-3'
```

Fluorescent Dyes

5' LCRed 640 labeled oligonucleotide (Roche Molecular Systems) is conjugated to the oligonucleotide post-synthesis. 5' LCRed 705 labeled oligonucleotide (Roche Molecular Systems) is conjugated to the oligonucleotide during the synthesis reaction, as a phosporamidite. 3' Fluorescein labeled oligonucleotide (Operon, Inc.), is purified by HPLC.

Reactions

An artificial system for the detection of initial template DNA copy number has been created from HPV 16 genomic DNA that had been previously cloned into a bacterial plasmid. The HPV 16 artificial template was produced by introducing an EcoRI restriction endonuclease site in the forward primer, and a BamHI restriction endonuclease site in the reverse primer. The PCR product was amplified from the HPV 16 plasmid to produce a sequence that could be readily cloned into a pUC19 plasmid.

Similarly, the internal quantification standard was created from the HPV 16 containing plasmid DNA using a combination of nested PCR primers. The design for creating this artificial sequence can be seen in FIG. 8. In summary, plasmid DNA containing HPV 16 genomic DNA top was amplified with PCR primers 900F16 and 1300R16. 16ICS is a long primer with an internal HPV 16 sequence that has been randomized. The DNA was then amplified with this primer to create the Internal Quantification Standard (IQS) sequence. This randomized region serves as the internal quantification standard probe-binding site. Primers 16RI9 and 16HI13 have been designed to introduce EcoRI and BamHI restriction endonuclease sites for directional subcloning of the final artificial sequence into a pUC19 plasmid. To ensure similar template backgrounds, HPV 16 was also amplified with the primers 16RI9 and 16HI13, to facilitate the directional subcloning of this amplicon into a pUC19 plasmid.

Producing the Artificial IQS and HPV 16 plasmids

HPV 16 plasmid DNA at $10^7$ copies per ÿl were aliquoted into 96-well microliter plates. Solutions containing the following final concentrations were prepared: 0.1 ÿM 16HI13 primer, and 0.1 ÿM of either 16RI9 primer or 16IQS primer, 50 mM Tris pH 8.3 (25° C.), 4.0 ÿM $MgCl_2$, 0.25 mg/ml Bovine serum albumin, 200 ÿM each dNTP, and KlenTaq DNA polymerase 0.2 Units/ÿl, 1:30,000 dilution of SYBR® Green I (Molecular Probes). Thermal cycling conditions for the amplification of the artificial HPV 16 and IQS, templates included 1 cycle of sample1 denaturation at 97° C. for 30 seconds. The amplification protocol included 30 cycles of denaturation at 90° C. for one second, annealing at 55° C. for 2 seconds, extension at 78° C. for 18 seconds with a fluorescence acquisition following extension. The ramp rates for each transition was set to the maximum of 20° C./second, except for the transition between the annealing and extension step at 10° C./second. Reactions were run on a 0.8% SeaKem Agarose gel (1×Tris, borate, EDTA, ethidium bromide) gel at 80 mA for 1.5 hours. The reaction products were visualized by UV light, and product bands were excised from the gel. The products were purified from the gels by AMICON™ (Amicon Plastics, Inc. of Houston TX.) Gel Nebulizers (Part No. 42600, Beverly, Mass.) according to the manufacturer's directions. Following purification, partial IQS template was subjected to a second round of amplification to complete the artificial IQS sequence. The reaction is the same as above, save for the template DNA, which was the partial IQS; and the primers 16RI9, and 16HI13. The final complete IQS sequence was band isolated from a 0.8% agarose gel, and purified as described above.

Purified artificial HPV 16 template, IQS template, and pUC 19 DNA were restriction endonuclease digested with Eco RI and Bam HI (Boehringer Manneheim Biochemicals) according to the manufacturers directions. Following digestion, DNA was band isolated on 0.8% Agarose gels and purified as described above. Purified template DNAs were ligated into the digested pUC19 DNA with T4 DNA ligase (Boehringer Manneheim Biochemicals) at 14° C. overnight. Ligated DNAs were transformed into competent E. coli DH5α cells, and plated onto Luria Broth Agar plates containing ampicillin at 125 μg/ml. Cells were incubated overnight at 37° C. Single colonies were isolated and grown in Luria Broth containing ampicillin at 125 μg/ml for 16 hours. Plasmids were isolated by Promega Wizard Minipreps. Final preparations were boiled for 5 minutes, and DNA concentration was determined by spectrophotometer readings at $A_{260}$ and $A_{280}$. Inserts were confirmed by amplification with the 900f16 and 1300r16 primers and FRET probe specificity pBECIQS or pBEC16.

Figure 6:
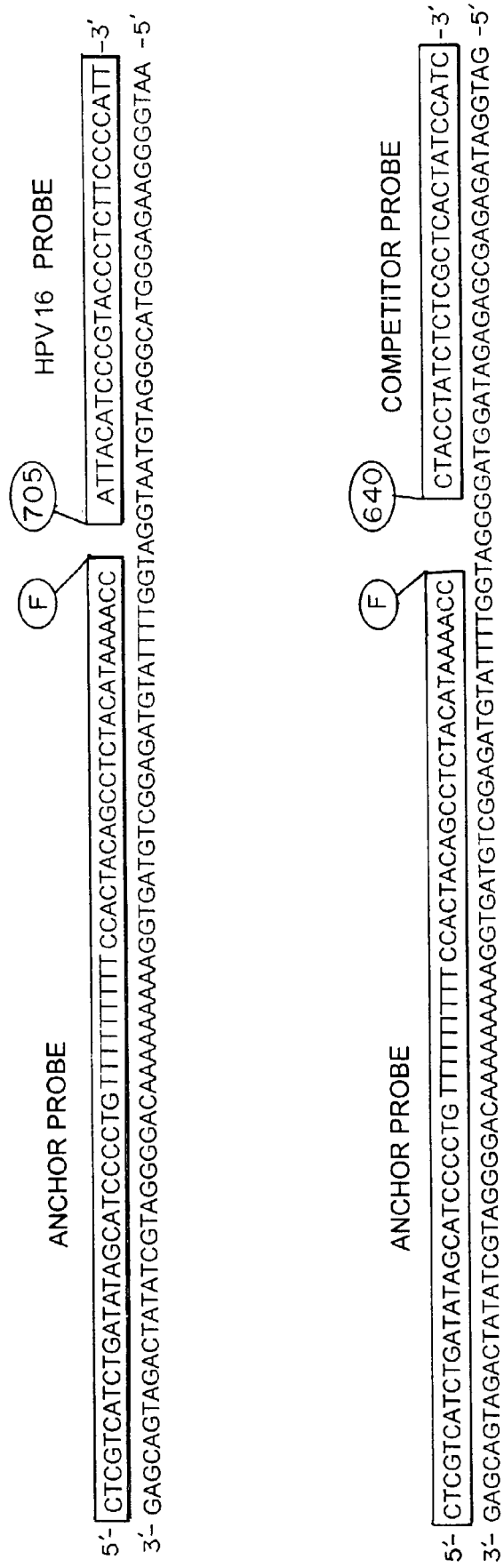
FIG. 6: represents the nucleotide sequences of the competitive DNA fragment for HPV 16 (SEQ ID NO. 5) and the targeting (SEQ ID NOS. 13 and 14), competitive (SEQ ID NO. 4) and anchor probes (SEQ ID NO 8)

The artificial IQS and HPV 16 templates served as the templates in all subsequent reactions. The design of the detection of the IQS product and the HPV 16 product is based around the objective of minimizing the differences between the target and the competitor DNAs. Both IQS and HPV 16 were amplified with a single primer set, 900f16 and 1300r16. A single fluorescein labeled "anchor" probe was used to position the FRET inducing fluorophore adjacent to the detection probes, as seen in FIG. 6. The detection probes are designed specifically to hybridized to either the IQS product, IQSp913, or to the HPV 16 product, 16p913. IQSp913 is an LCRed 640 labeled probe that can be detected in Channel 2 of the LIGHTCYCLER®. 16p913 is an LCRed 705 labeled probe that can be detected in Channel 3 of the LIGHTCYCLER®. This internal standard design allows for simultaneous amplification of both the competitor and target DNA in a single reaction cuvette, as well as providing a color-based method for distinguishing the two products.

Figure 9:
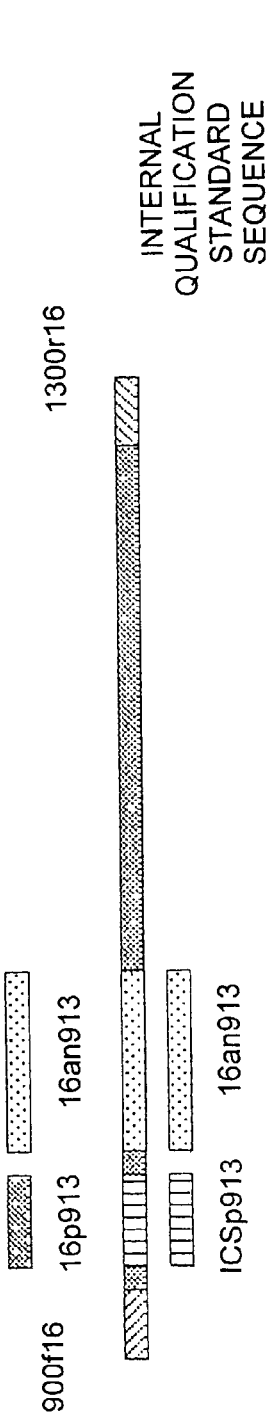
FIG. 9: is a diagrammatical representation of the hybridization probes used to detect the internal quantification standards and the HPV 16 artificial template.

FIG. 9 illustrates detection of internal quantification standards (IQS) and the HPV 16 artificial template. A single primer pair was designed to amplify the BPV 16 artificial template (900f16/1300r16). This same primer pair also amplifies the internal quantification standard sequence. A 58-mer fluorescein labeled oligonucleotide (16an913), that exactly matches both the artificial HPV 16 and IQS sequences, serves as the FRET anchor. Two additional probes were designed, one to specifically detect the HPV 16 sequence (16p913) and the other for detecting the IQS sequence (ICSp913).

Amplifications for quantification analysis

Serial dilutions of plasmid pBECIQS and plasmid pBEC 16 were made. DNA templates were aliquoted and mixed into 96-well microtiter plates. Master mix solutions for the quantification contained the following final concentrations: 0.4μM 900f16 primer, 0.1 μM 1300r16 primer, 0.3 μM of 16an913 fluorescein probe, 0.1μM of each 16p913 LCRed 705 and IQSp913 LCRed 640 probes, 50 mM Tris pH 8.3 (25° C.), 3.25 μM $MgCl_2$, 0.25 mg/ml Bovine serum albumin, 200μM each dNTP, and Taq DNA polymerase 0.2 Units/μl. Thermal cycling conditions for the amplification of the internal quantification standard and the artificial HPV 16 DNA templates included 1 cycle of sample denaturation at 97° C. for 30 seconds. The amplification protocol included 50 cycles of denaturation at 92° C. for 1 second, annealing at 47° C., fluorescence acquisition following a hold at 5° C. for 6 seconds and extension at 78° C. for 12 seconds. The ramp rates for each transition was set to the maximum of 20° C./second, except for the transition between the annealing and fluorescence acquisition step that was at 0.4° C./second.

Results

Figure 10:
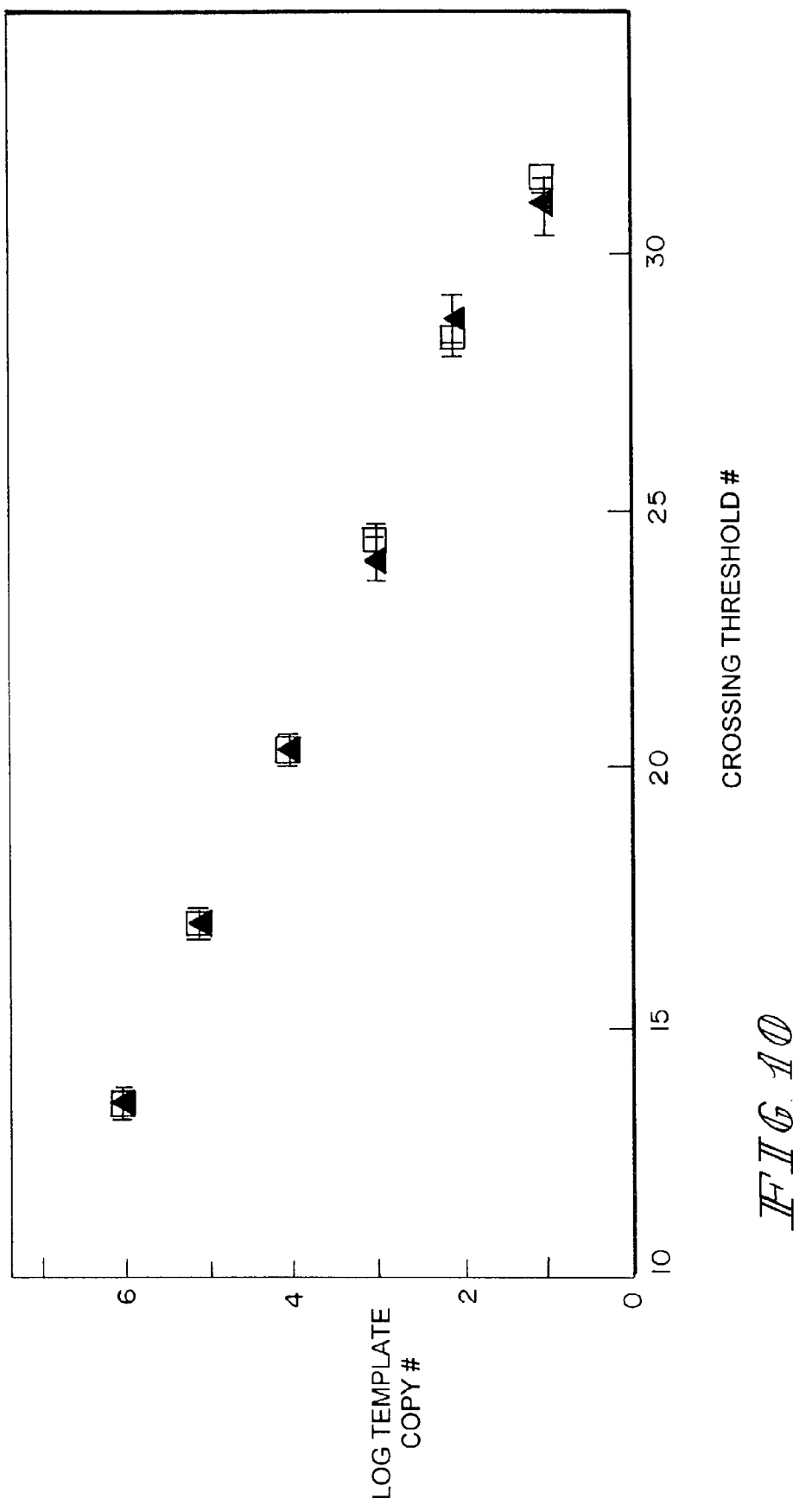
FIG. 10: is a graphic representation of the detection efficiency of the Internal Quantification Standard (▲) and Artificial HPV 16 template (□). The data are presented as the average of at least three separate data points, with standard deviations for each.

As indicated above in the derivation of the delta C.T. equation, the detection efficiency of both the target and internal quantification standard DNAs should be equal. To determine whether, in fact, this is met by this system, the crossing threshold for either HPV 16 or the IQS was determined in reactions where both probes were present and only one DNA template was available for detection. As seen in FIG. 10, the crossing thresholds for both the target and competitor DNA are similar. FIG. 10 shows the crossing threshold of the amplification curves following color compensation, baseline subtraction, setting of the noise-band, and finally detecting the cycle threshold at which the amplification curves can be detected. Although the amplification or detection efficiency of these reactions is not linear over the range of concentrations tested, the crossing thresholds are consistent for both the internal quantification standard and the target DNA.

FIG. 10 shows the detection efficiency of Internal Quantification Standard and Artificial HPV 16 template. The data are presented as the average of at least three separate data points, with standard deviations for each.

Figure 11A:
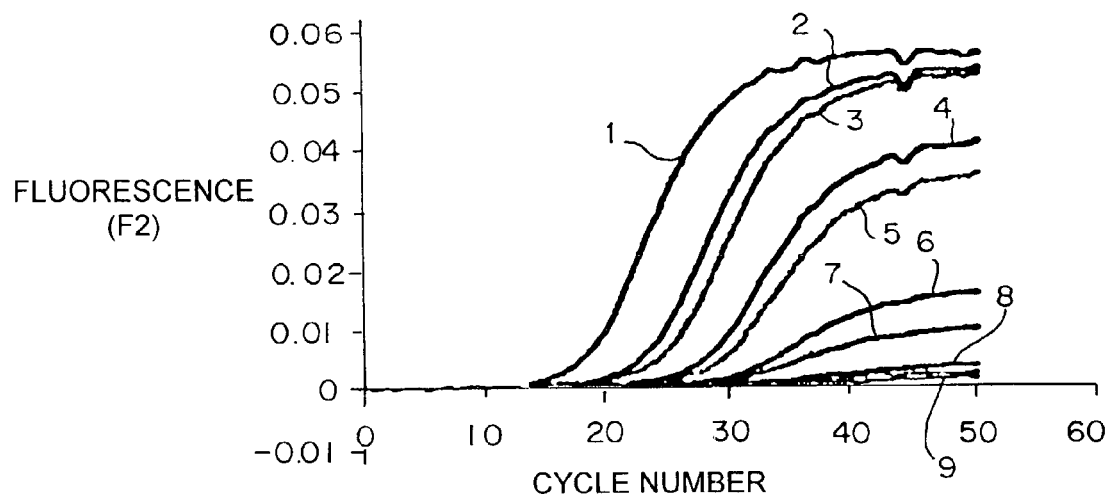
FIGS. 11a-b: illustrate a typical internal control reaction demonstrating fluorescent data from an internally controlled hybridization probe reaction. Internal quantification standards at concentrations of $1 \times 10^9$ (1); $5 \times 10^8$ (2); $1 \times 10^8$ (3); $5 \times 10^7$ (4); $1 \times 10^7$ (5); $5 \times 10^6$ (6); $1 \times 10^6$ (7); $5 \times 10^5$ (8); $1 \times 10^5$ (9) are plotted in FIG. 11a. HPV 16 at $1 \times 10^6$ in each of the samples is shown in FIG. 11b.
Figure 11B:
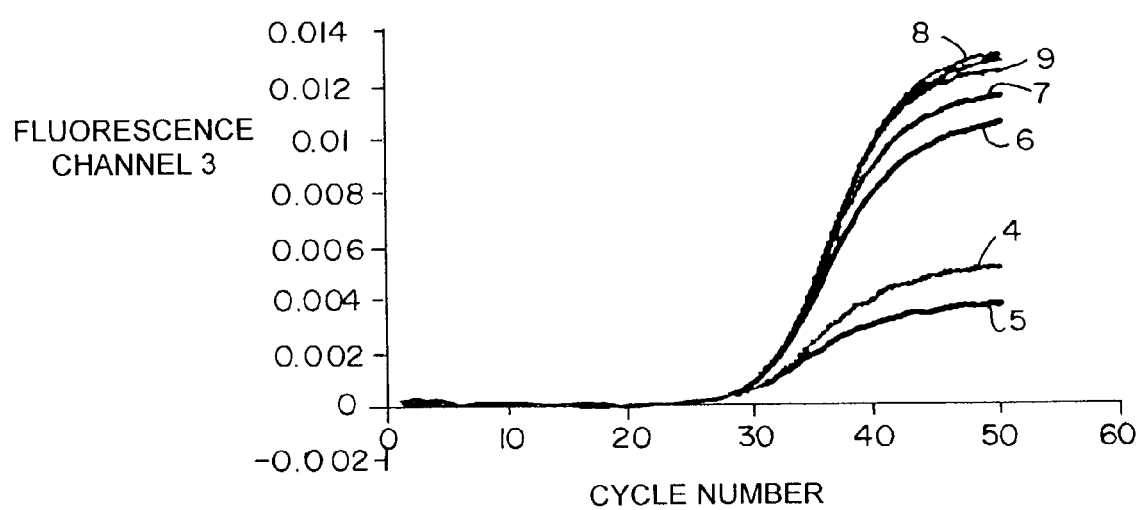

A typical internal control reaction is depicted in FIGS. 11a and 11b. Serial dilutions of the IQS template were prepared ($1 \times 10^9$, $5 \times 10^8$, $1 \times 10^8$, $5 \times 10^7$, ... $1 \times 10^3$). Each sample contained $1 \times 10^6$ initial copies of HPV 16 target DNA, and was spiked with one of the serial dilutions of the competitor IQS DNA. The internal standard is detected in channel two (FIG. 11a), the decreasing concentrations of IQS show a typical crossing threshold cycle shift as the initial number of template copies decreases. In FIG. 11b, HPV 16 DNA is shown as detected in channel 3. As expected with a single concentration of initial template DNA, $1 \times 10^6$, the cycle threshold of detection is consistently at cycle 28. The data in FIGS. 11a and 11b have been compensated for color overlap from channel 2 into channel 3, using a color compensation file.

Figure 12:
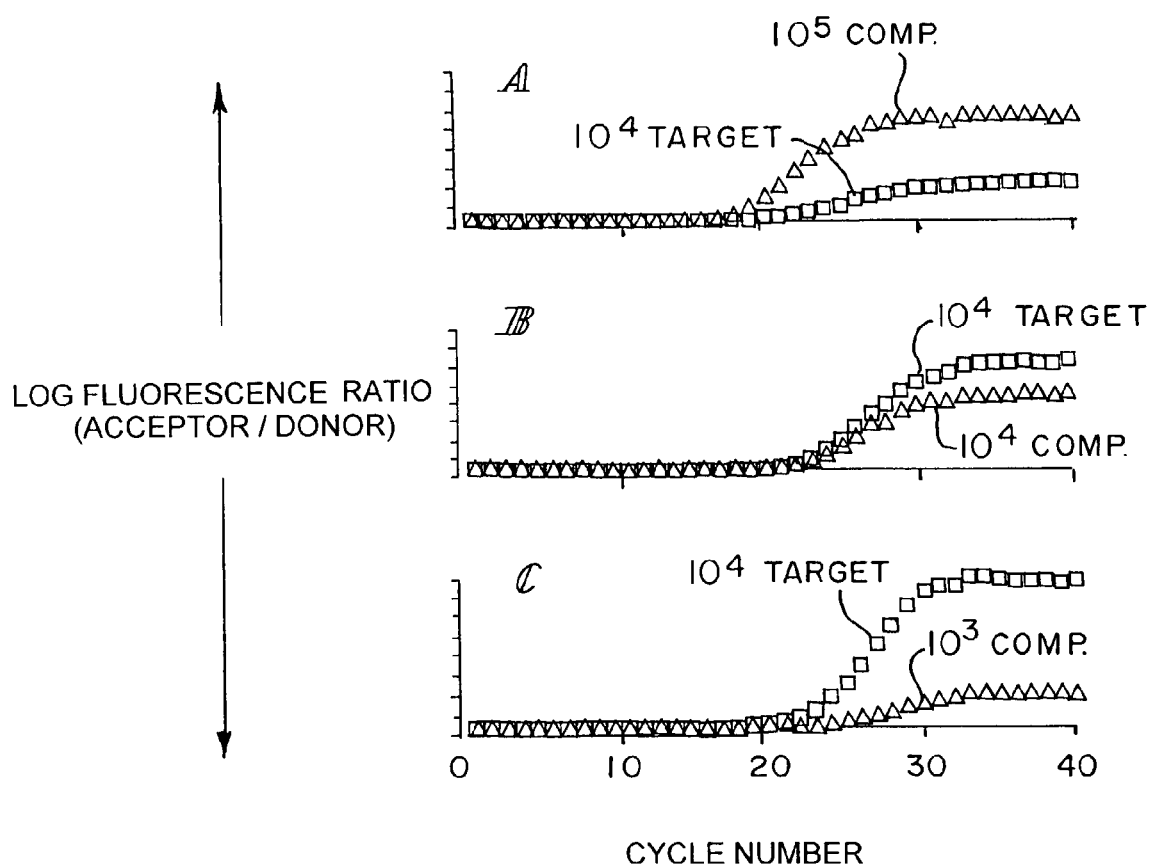
FIGS. 12a-c: are graphic representations of the detected fluorescence vs. cycle number for the Internal quantification standard (open triangles) and HPV 16 (closed squares). In each case HPV 16 is at an initial template concentration of $1 \times 10^4$. The internal quantification standard is at initial template concentrations of $1 \times 10^5$ (FIG. 12a), $1 \times 10^4$ (FIG. 12b), and $1 \times 10^3$ (FIG. 12c)

The cycle shift that occurs during the amplification when differing initial copies of target DNA and competitor DNA are present is regularly observed in reactions where one DNA template is maintained at a single starting copy number and the other template is varied. In FIGS. 12a-c, an example of a typical cycle shift is presented. Three reactions are represented. Each reaction comprises the templates and the probes for IQS and HPV 16 amplification and detection. Internal quantification standard (triangles) and HPV 16 (squares) are multiplexed. In each case, HPV 16 is at an initial template concentration of $1 \times 10^4$. The internal quantification standard is at initial template concentrations of $1 \times 10^5$ (FIG. 12a), $1 \times 10^4$ (FIG. 12b), and $1 \times 10^3$ (FIG. 12c). Accordingly, the initial copies of IQS DNA range from ten fold greater than the HPV 16 (FIG. 12a), to ten fold less than the HPV 16 DNA (FIG. 12c). As can be seen in FIG. 12b, where the initial copy number of both the target and the competitor DNAs are the same, the crossing thresholds are identical. However, when the competitor is either ten fold greater (FIG. 12a) or ten fold less than (FIG. 12c) the cycle threshold for the internal quantification standard is earlier or later, respectively, than the cycle threshold for the HPV 16 DNA.

Figure 13:
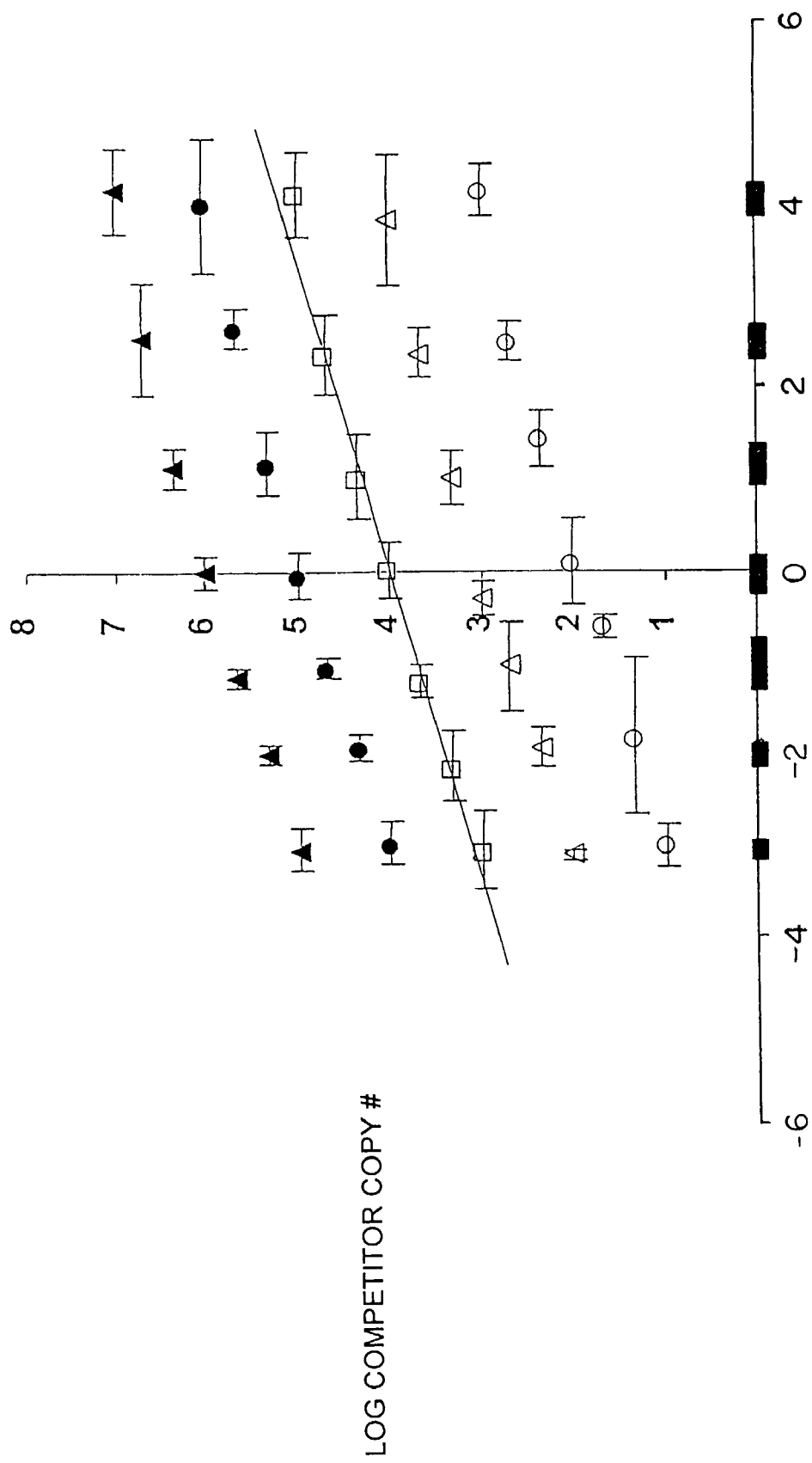
FIG. 13: is a graphic representation of the log of initial competitor copy number versus difference in crossing threshold (delta C.T.): A graph of internal quantification standard reaction with distinct concentrations of HPV 16 artificial template. HPV 16 initial template concentrations are: $1 \times 10^2$ (open circles), $1 \times 10^3$ (open triangles), $1 \times 10^4$ (open squares), $1 \times 10^5$ (closed circles), $1 \times 10^6$ (closed triangles). Error bars are determined from the standard deviation from four independent reaction data points. The 95% confidence interval at each ratio of competitor to target is indicated on the x-axis.

The cycle shift for copy number differences between the competitor DNA (IQS) and the target DNA (HPV 16) was plotted as the change in cycle threshold, between the IQS in channel 2 and the HPV 16 in channel 3, versus the log of the initial copy number of the IQS in the reaction. FIG. 13 represents the data from two separate experiments for each target, HPV 16, DNA concentration each performed in triplicate. HPV 16 initial template concentrations are: $1\times10^2$, $1\times10^3$, $1\times10^4$, $1\times10^5$, and $1\times10^6$. Error bars are determined from the standard deviation from four independent reaction data points. The standard deviations are hence a combination of intra- as well inter-experimental variation. The majority of the cycle threshold error arises from inter-experimental variation. The lines plotted represent the trendlines for the averaged delta C.T. data points for each IQS and HPV 16 concentration. A trendline for the averaged delta C.T. data points for each IQS concentration and the $1\times10^4$ HPV 16 concentration is shown in FIG. 13. The trendlines are calculated from a least squares analysis of the best linear fit to the points. Table 2 presents the equations for the linear fit to the trendlines.

The analysis of delta C.T. data from internal quantification standard curves is shown in Table 2. The trendline equations used to calculate target concentrations are shown with the log $[T_o]$ indicated in bold. Amplification efficiencies and the actual and calculated concentrations of HPV 16 target DNA are also indicated.

TABLE 2

Figure 8:
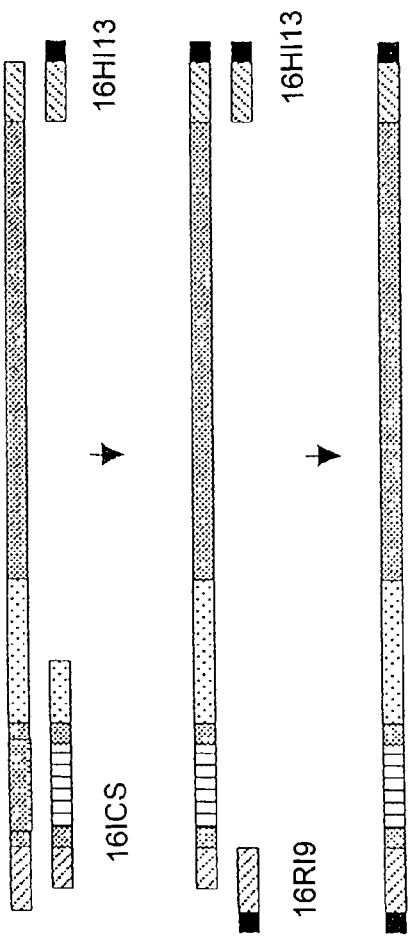
FIG. 8: is a diagrammatical representation of the strategy used to create the competitive DNA fragment for HPV 16.

Linear best-fit trend line to the data in FIG. 8.

| Trendline Equation $\log C_o = \log E(@n) + \log T_o$ | Efficiency | Calculated Copy # | Actual Copy # | % Error* |
|---|---|---|---|---|
| y = 0.2802x + 5.9347 $R^2 = 0.989$ | 1.91 | $0.86 \times 10^6$ | $10^6$ | 13.96 |
| y = 0.2872x + 4.9235 $R^2 = 0.9911$ | 1.94 | $0.84 \times 10^5$ | $10^5$ | 16.15 |
| y = 0.2826x + 3.9527 $R^2 = 0.988$ | 1.92 | $0.90 \times 10^4$ | $10^4$ | 10.32 |
| y = 0.2944x + 2.9621 $R^2 = 0.9885$ | 1.97 | $0.92 \times 10^3$ | $10^3$ | 8.36 |
| y = 0.289x + 1.8822 $R^2 = 0.9922$ | 1.95 | $0.76 \times 10^2$ | $10^2$ | 23.76 |

*The absolute difference between the observed copy # and calculated copy # is represented as the % Error for each particular initial target copy #.

The log of the slopes of each of these lines was calculated to produce the average reaction efficiency, and the log of the y-intercept was used to calculate the observed target DNA concentration. The observed target concentrations were in each of the samples no greater than 24 percent varied from the estimated concentration based on limiting dilution determination of the DNA concentration and subsequently the initial template copy number in each reaction.

The use of a common set of primers to amplify similar templates and two hybridization probe systems to detect the products of those templates apparently results in samples that have similar crossing thresholds. The application of this two color detection system to internal quantification standards has been facilitated by the derivation of an equation that uses only a simple manipulation of the crossing threshold data to produce internal quantification with a minimum dynamic range of 10 fold on either side of the target DNA concentration.

While the above examples have incorporated FRET oligonucleotide probe systems, it is understood that other probe systems may be used within the scope of this invention. For example, single-labeled oligonucleotide probes may be used, eliminating the need for the anchor probe. The following example uses both the FRET oligonucleotide probe system (Sensor and Acceptor) and the single-labeled probe system (Sensor probe only).

EXAMPLE 6

This example demonstrates that ratios between different nucleic acid targets in a mixture can be quantified using a Thermodynamic Modeling based Signal Processing algorithm. In an exemplary bi-allelic system, allele fractions as low as 1 part in 100 can be determined accurately by aid of this algorithm. This method can be used, for example, to determine allelic patterns of gene expression, allele frequencies in pooled populations, and ratios between different cell types in a mixed tissue sample.

Model Bi-allelic System

A single nucleotide polymorphism (SNP) locus in the human p53 gene (GENBANK#, computerized storage and retrieval services dealing with information relating to nucleic acid sequence data, Accession U94788) is used as target. Detection and analysis of the SNP locus is possible by a 3'-fluorescein-labeled Sensor Probe (5'GTTCCTG-CATGGGCGGCATGAAC-F (SEQ ID NO.9)). When matched perfectly to the wild-type target sequence, this probe has a Tm of 70° C. When hybridized to the mutant allele, probe Tm is shifted to about 62° C. due to the GA mismatch at position 12 from the 5' end of the probe.

This Sensor Probe can be used alone to detect the SNP locus through the fluorescence quenching mechanism in which the signal of the probe decreases upon hybridization by the effect of a G residue on the target strand (See Crockett and Wittwer. *Anal Biochem.* 2001, 290(1):89-97). Signal change is observed in the F1 channel of the LIGHTCYCLER® apparatus. Illustratively, this probe can also be paired with an Acceptor Probe that is labeled with a fluorescence resonance energy acceptor dye, LCRed 640, at its 5' end (5'640-GGAG-GCCCATCCTCACCATCATCACAC TGGAAG (SEQ ID NO.10), Tm=75° C). Signal change from this FRET pair probe system is observed in the F2 channel.

Target Preparation

Targets with wild-type and mutant alleles are generated by PCR using Forward primer 5' GCGCACTGGCCTCATCTT (SEQ ID NO.11) (Tm=62.9° C.), and Reverse primer 5' GGT-CAGCGGCAAGCAGA (SEQ ID NO.12) (Tm=62.6° C.). The amplified samples are purified, quantified spectrophotometrically, and mixed at various known molar ratios.

Melting Curve Analysis

Figure 16A:
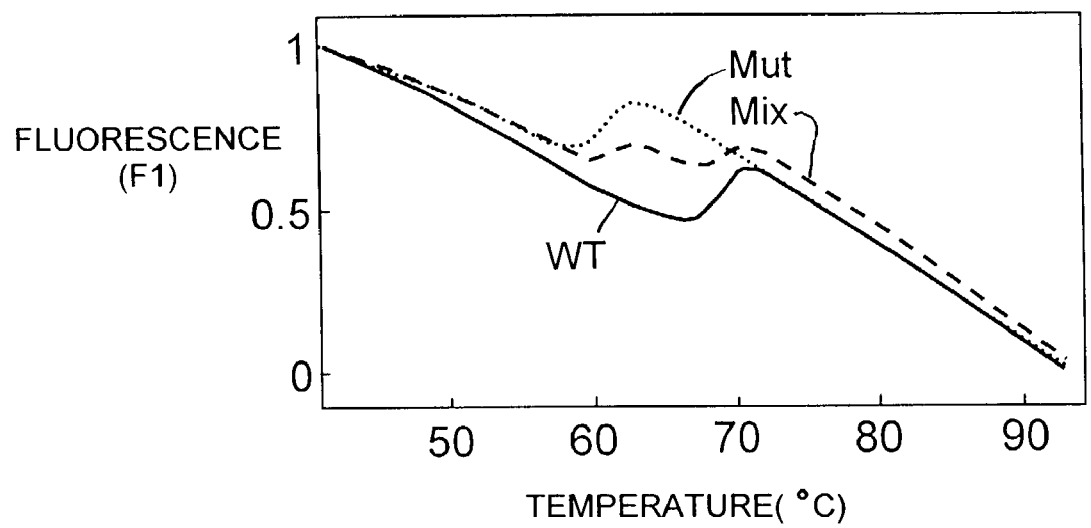
FIGS. 16a-d: are plots of melting analysis of a wild type (WT) sample ( - - - ), a mutant (Mut) sample ( . . . ), and a mixture (Mix) of wild and mutant alleles at 50:50 ratio ( - - - ), detected by the Sensor probe only (FIGS. 16a, and b), or with the FRET pair probes (FIGS. 16c, and d)

The reaction mixture consists of DNA (2000 copies/10μL), KlenTaq enzyme (0.8 U/10μL), TaqStart antibody (0.088 μg/10μL), 0.2 mM dNTP, 1X PCR buffer including 3 mM Mg$^{++}$ (Idaho Technology Inc., UT), and 0.2 μM of the Anchor probe and/or the Sensor probe. Unlike Example 4, it is not necessary to use a high amount of probe as the heterozygote sample in this system provides a melting peak area ratio of about 1. Thermal cycling conditions are 94° C. (reached by a transition rate of 20° C./s, held for 0 seconds); 56° C. (transition rate of 20° C./s, held for 5 seconds); 74° C. (transition rate of 2° C./s, held for 7 seconds). After forty PCR cycles, melting curve analysis is conducted by denaturing the sample at 94° C., annealing at 40° C., and melting the double-stranded DNA using a ramp rate of 0.2° C./s. Fluorescence is monitored continuously during melting. The resulting melting curve data (shown as example in FIGS. 16a and 16c for allele ratio of 50:50, and FIGS. 17a, 17c for allele ratio of 95:5) are directly analyzed with the Thermodynamic Modeling based Signal Processing (TMBSP) software, and allele ratios estimated. Two external standards (100% of wild type allele, and 100% mutant allele) are provided for the TMBSP analysis method. For estimations of allele fractions using the peak area ratio method, first the melting curve data are converted into melting peak data by taking the negative first derivative (shown as example in FIGS. 16*b*, 16*d* for allele ratio of 50:50, and FIGS. 17*b*, 17*d* for allele ratio of 95:5). The data are then analyzed as described in Example 4, using software such as the LCDA Software (Roche Molecular Biochemicals).

Thermodynamic Modeling Based Signal Processing (TMBSP) Algorithm

This algorithm couples digital signal processing with a thermodynamic observation to calculate the mass fractions of materials in a mixture. Digital signal processing is performed using Fast Fourier Transformations and by associating small amplitude Fourier modes with noise in the signal. The thermodynamic modeling is based on the Gibbs free energy of a mixture, and assumes that there are no chemical interactions between melted materials. Additionally, the algorithm includes the ability to analyze the melting signal of a mixed sample in the absence of standards. The method provides the melting temperature and the fraction of the unknown components.

Prior technologies differ from the illustrative method in four ways. First, most technologies perform the signal processing using Fourier-based deconvolution to identify individual components of a signal that is composed of many different species. These methods assume the input signal is a convolution of the individual signals with a predetermined convolution kernal. Examples of this type of method are found in U.S. Pat. Nos. 5,273,632, 5,748,491, and 5,346,306. Illustrative methods of this disclosure determine the deconvolution kernal as a component of determining the mass fractions of the materials.

Second, prior technologies determine the desired quantities one at a time. Once a component of the signal is determined, these methods subtract the result from the signal and determine the next component. An example of this type of technology is found in U.S. Pat. No. 5,985,120. The methods of this disclosure determine the mass fractions with an "all at once" approach.

Third, prior technologies using digital signal processing have been involved in the analysis of images of PCR amplified samples on an electrophoretic gel or similar devices, as in U.S. Pat. Nos. 5,906,919, 5,912,165, 6,066,459 and 6,054,268, or with mass spectrometry as in U.S. Pat. Nos. 6,054,268, or 6,268,131. The methods of the present invention do not require post-amplification manipulation of the PCR samples.

Fourth, prior technologies using digital signal processing in PCR based applications, such as U.S. Pat. No. 6,221,600, do not use thermodynamic modeling.

The present invention couples the process of determining a set of desired material parameters and simultaneously determining an optimal signal processing scheme.

Digital signal processing with the Discrete Fourier Transform (DFT) has been widely used since the discovery of the Fast Fourier Transform (FFT). The basic idea is to represent the signal as a linear combination of sinusoidal signals (or basis functions), and to keep only those sinusoidal basis functions that contain reliable information about the signal.

A DFT uses a finite number of terms from a Fourier series to approximate a periodic function. The Fourier series can represent periodic function with a reasonable amount of smoothness. Suppose f(T) is a fluorescence melting signal, then the Fourier series of f(T) is $$f(\tau) = \sum_{k=-\infty}^{\infty} g(k) e^{2\pi i k \tau}$$

where the temperature is rescaled by the change of variables $$\tau = \frac{T - T_{min}}{T_{max} - T_{min}}$$

The variables g(k) are the discrete Fourier coefficients of f(T). Each coefficient g(k) is calculated by computing the integral $$g(k) = \frac{1}{\pi} \int_0^1 f(\tau) e^{2\pi i k \tau} d\tau$$

and the FFT is an efficient method of computing a set of these integrals.

In practice, only a finite number of these terms can be computed, and some terms are meaningless because they represent noise in the signal. The DFT provides a simple method of eliminating the noise from a signal by setting those discrete Fourier coefficients associated with the noise equal to zero. One is left to decide which coefficients correspond to noise and which correspond to signal.

A mathematical truism is useful to accomplish this. The sum of the moduli of the discrete Fourier coefficients is equal to the norm of the function f(T), or $$\|f(\tau)\|^2 = \sum_{k=-\infty}^{\infty} |g(k)|^2$$

Assuming the noise in the signal is small, a common and safe method of eliminating noise is to use this property and keep enough terms of the DFT so the norms of the actual signal and processed signal are close to one another. Specifically, one sets g(k)=0 if |g(k)|<σ where σ is a small tuning parameter. If K(σ) is the set of discrete Fourier coefficients that have not been set to zero, then the processed signal is $$f^\sigma(\tau) = \sum_{k \in K(\sigma)} g(k) e^{2\pi i k}$$

and it has the property that the processed signal is close to the actual signal since $$\left\| f(\tau) - \sum_{k \in K(\sigma)} g(k) e^{2\pi i k} \right\|$$

is small by construction. Additionally, the periodic basis functions that only contribute a small amount to the actual signal are ignored. Usually these basis functions oscillate rapidly and are identified with noise. This procedure has the added benefit that it approximates the actual signal with a small set of data. The only data that need to be stored are the wave numbers in the set $K(\sigma)$ and the corresponding discrete Fourier coefficients.

Thermodynamic Modeling:

The fluorescence signal of a PCR product decreases or increases when the product denatures. This process is a phase transition that can be understood using thermodynamics. The thermodynamics of phase transitions of a mixed material are based on the thermodynamics of a phase transition of the base substance.

Consider a mixture of many substances, labeled 1, 2, ..., N. If $G_i(T)$ is the Gibbs free energies of substance i as a function of temperature, then the Gibbs free energy of a mixture of these substances is given by $$G_{mix} = \sum_i m_i G_i(T) + \sum_{i>j} \Delta G_{mix,ij}$$

where $m_i$ is the mass fractions of the substance i. The energy from mixing is $\Delta G_{mix}$ and it accounts for changes in entropy introduced by mixing species i and j. In aqueous solutions, this term is usually small.

Fluorescence melting signals do not measure the Gibbs free energy of a material. However, since the signals are monotonically changing as a function of temperature, temperature itself can be thought of as a function of fluorescence, i.e. T(f) where f is the fluorescent melting signal.

This is a useful observation since $G_i(T)$ is typically a monotone function of temperature, particularly at temperatures near a phase transition. Since temperature is a function of f, composing $G_i(T)$ with T(f) implies that $G_i$ is a function of fluorescence. Finally because $G_i$ is a monotone function one can think of fluorescence as a function of $G_i$.

These observations suggest that one can model the fluorescence of a PCR mixture as $$f_{mix} = \sum_i m_i f_i(T) + \sum_{i>j} \Delta f_{mix,ij}$$

where $f_i$ is the fluorescence melting signals of species i, and where $f_{mix}$ is the fluorescence melting signals of the mixture of species i with j.

Given the fluorescence melting signals, $f_i$, $f_{mix}$, and ignoring the fluorescence mixing terms, a good approximation for the mass fractions of the substances can be found by minimizing the following objective function over all choices of m, between zero and one.

$$\int_{T_0}^{T_1} \left\| f_{mix} - \sum_i m_i f_i(T) \right\| dT$$

Basis Function Approximation

Figure 20:
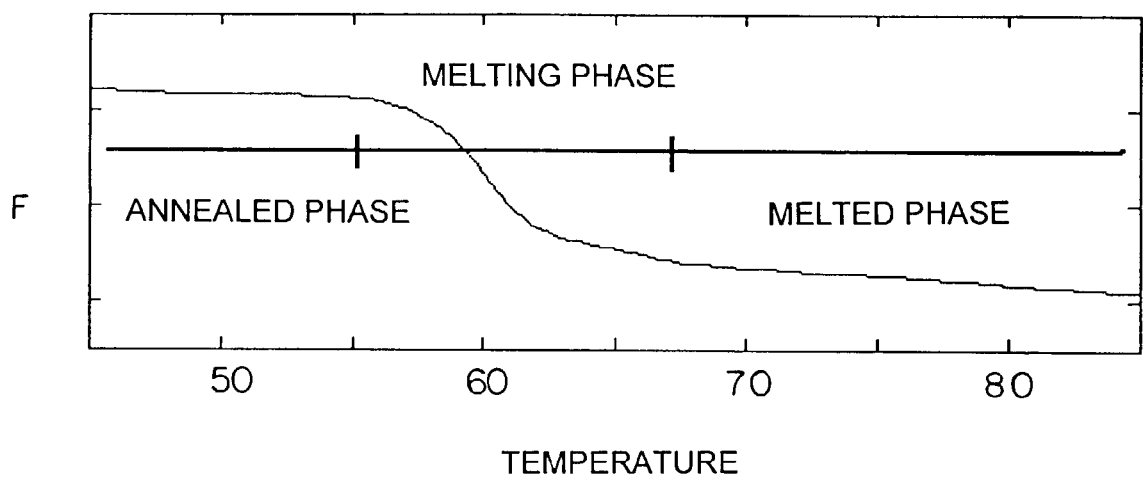
FIG. 20: is a graphic representation of a model melting curve which has three phases: the non-linear "annealed phase," the melting transition (depicted as the "melting phase"), and the linear "melted phase." The basis function approximation algorithm is based on this model to approximate the melting curve.

The fluorescence melting signal to be analyzed may or may not have standard melting signal such as $f_i$ described above. When the standard signals are missing, they must be approximated. The illustrative approximation scheme is based on the observation that the fluorescence melting signal of the products is essentially linear at temperatures greater than the melting transition (i.e. at the "melted phase"), and non-linear at temperatures less than the melting transition (i.e. at the "annealed phase," see FIG. 20).

To approximate the standard signals, the fluorescence melting signals of all PCR mixtures are scaled relative to one reasonable signal, and an approximation of the remainder data is calculated. The mathematical model used is:

$$f^r(T) = P_1(T)\left(1 - \sum_j m_j M_j(T)\right) + P_2(T) \sum_j m_j M_j(T)$$

and the terms in the model are defined as the following:

T—temperature $f^r(T)$—approximated fluorescence of the melting curve $P_1(T)$—nonlinear function representing the fluorescence in the annealed phase $P_2(T)$—linear polynomial representing the fluorescence in the melted phase $M_j(T)$—fraction of species j that has melted; $M_j(T)=0$ implies species j is annealed and $T_j$ is the melting temperature $m_j$—constant mass fraction of species j in the sample vessel Finally all the summations in the model include N terms, with one term for each melt.

The model was constructed using a combination of observed behavior and elementary thermodynamics. The background terms $P_j(T)$ are solely based on experience with the data, while the linear combinations of the fractional melting equations are based on the free energy of a mixture of materials. The free energy is equal to the sum of the free energies of the components of the mixture to first order. Changes in the free energy of the materials are the driving force for a phase transition in the probe-melting experiments, therefore, it is expected that the fluorescence of the samples will be nearly linear combinations of the fluorescence of the individual species. In this context, the terms Mj(T) represent the probability that a type j probe is attached to its target. The melting terms $M_j(T)$ depend on two parameters: the melting temperature $T_j$ at which the curve is steepest in the melting transition, and the width of the melting transition wj.

Algorithm Coupling

In the first step of the full algorithm, scaling is performed, and the samples with no melting signal ("negatives") are found. Then parameters that specify the remainder functions are found. Finally an iterative process adds one remainder at a time, and minimizes the objective function $$\min_{m_i, \sigma} E(m_i, \sigma, T_j) = \int_{T_0}^{T_1} \left\| f_{mix}^\sigma - \sum_i m_i f_i^\sigma(T) - f^r(T) \right\| dT$$

to simultaneously find the smoothing parameter $\sigma$, the mass fractions of the known standards $m_i$, and the melting temperature and mass fraction parameters of the remainder functions, $T_j$ and $m_j$. The iterative process is terminated when the mass fractions sum are bigger than 1-$\epsilon$ where $\epsilon$ is a tolerance, and when the approximated melting signal of the mixed material is sufficiently close to $f_{mix}$. The previously computed results serve as inputs to the optimization software that minimizes the objective function. The tolerance limit g used in the algorithms is proportional to the relative size of the noise in the signal. Other methods of selecting the tolerance could be used.

Figure 18:
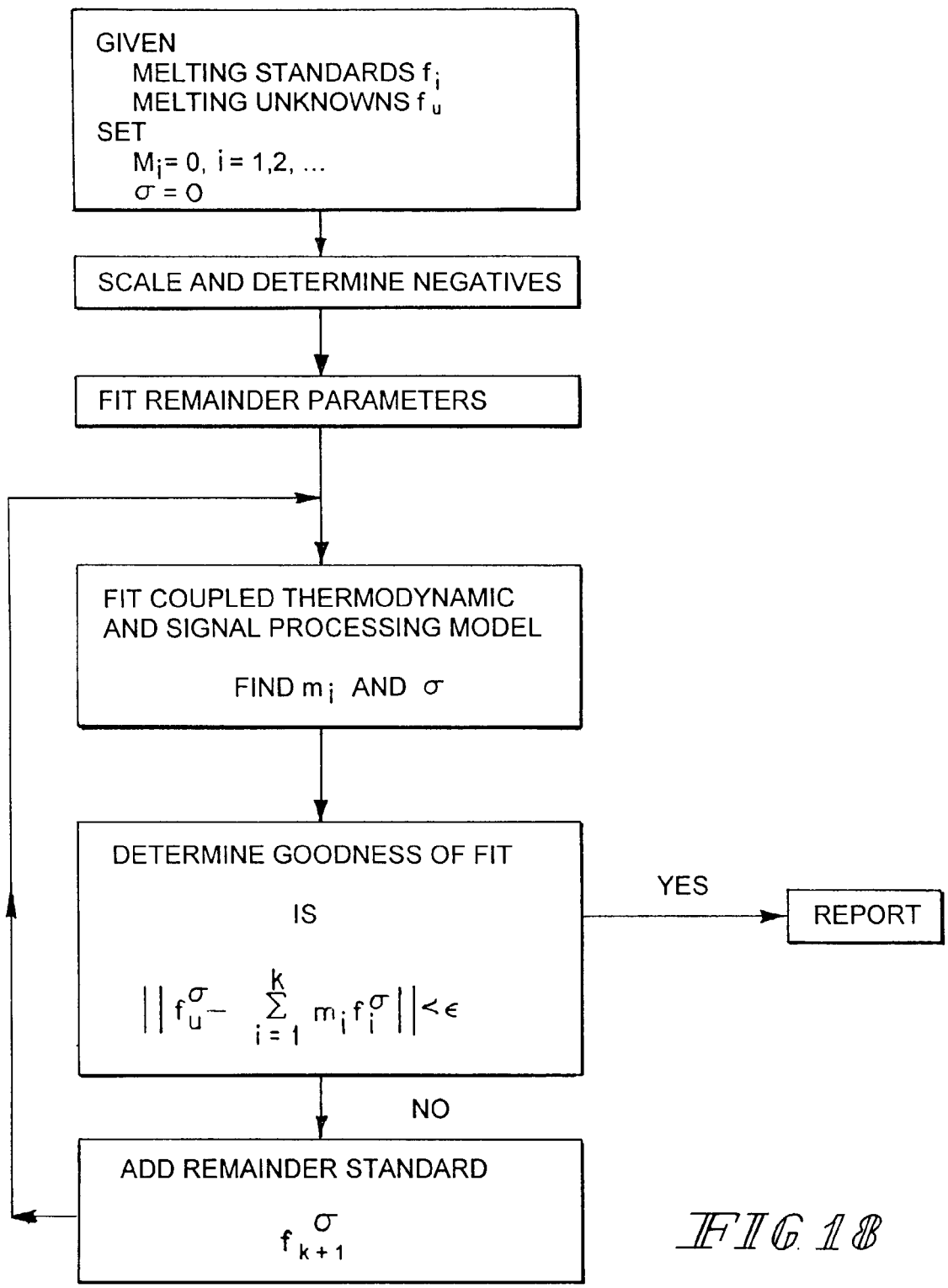
FIG. 18: is a flow chart of the Thermodynamic Modeling based Signal Processing algorithm.

A flow chart of the full algorithm process is shown in FIG. 18. The top box is the entry into the algorithm, and users specify the standards and unknowns. The second box determines the scale factors of all the signals and determines whether any of the signals are negatives. The third box signifies where the parameters of the remainder function are determined. If combinations of the standards adequately model the unknown melting curve, then the remainder parameters will be zero. In the absence of known standards $f_i$, then the approximated curves f will be used exclusively.

Figure 16B:
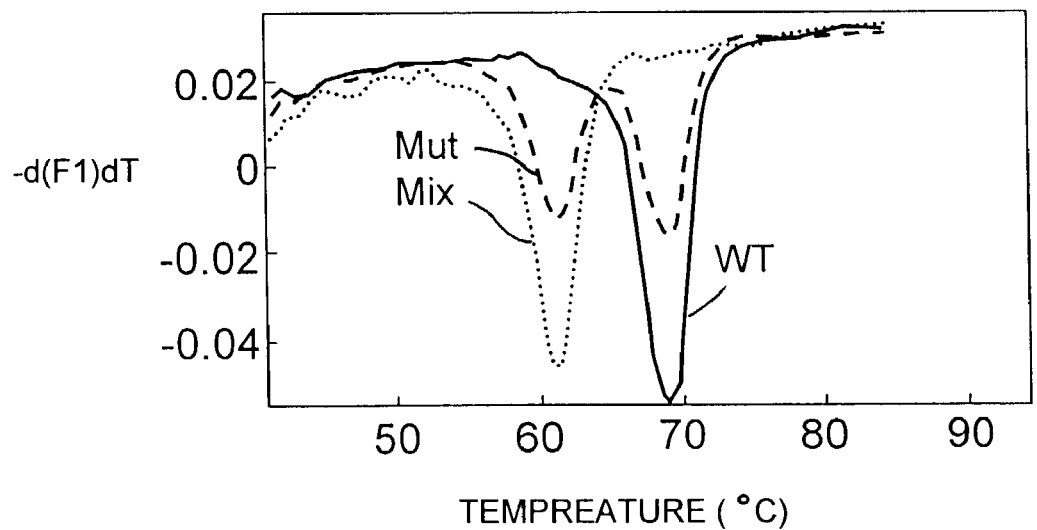
Figure 16C:
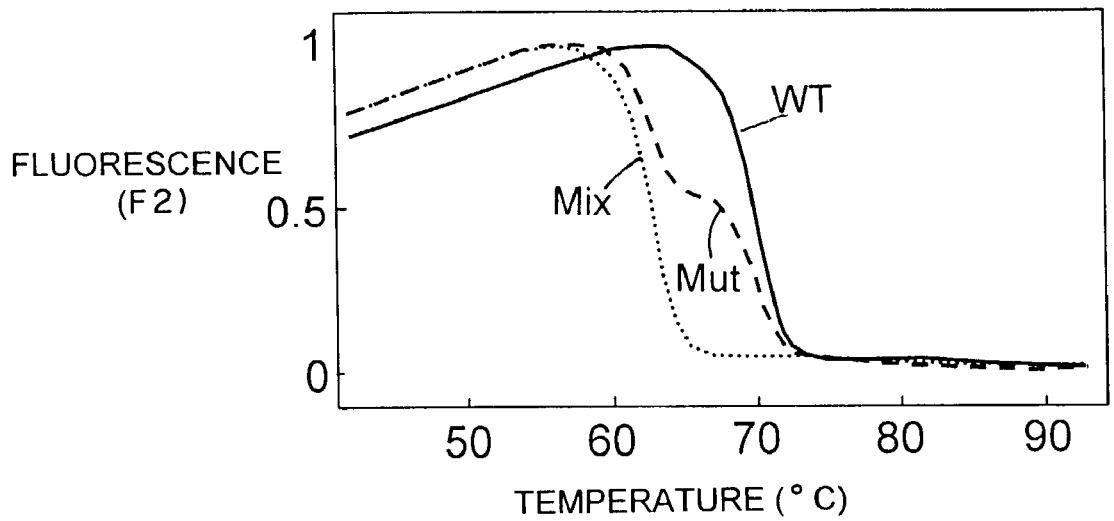
Figure 16D:
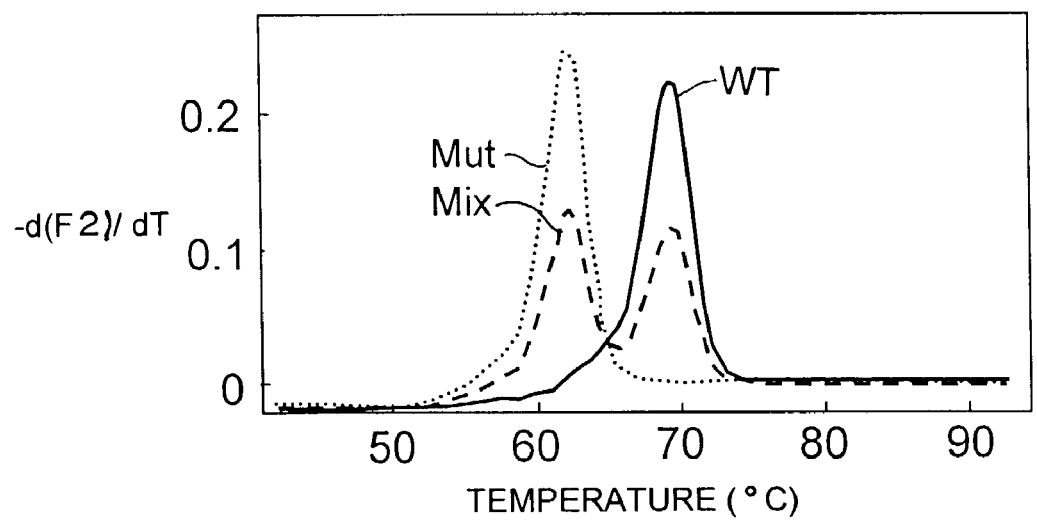
Figure 17A:
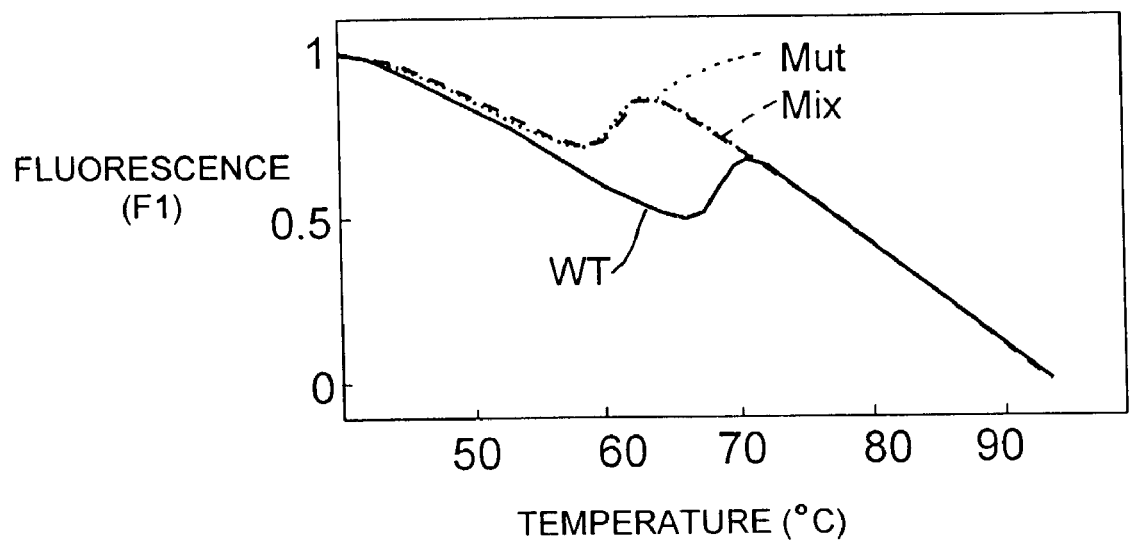
FIGS. 17a-d: are plots of melting analysis of a wild type (WT) sample ( - - - ), a mutant (Mut) sample ( . . . ), and a mixture (Mix) of wild and mutant alleles at 95:5 ratio ( - - - ), detected by the Sensor probe only (FIGS. 17a, and b), or with the FRET pair probes (FIGS. 17c, and d)
Figure 17B:
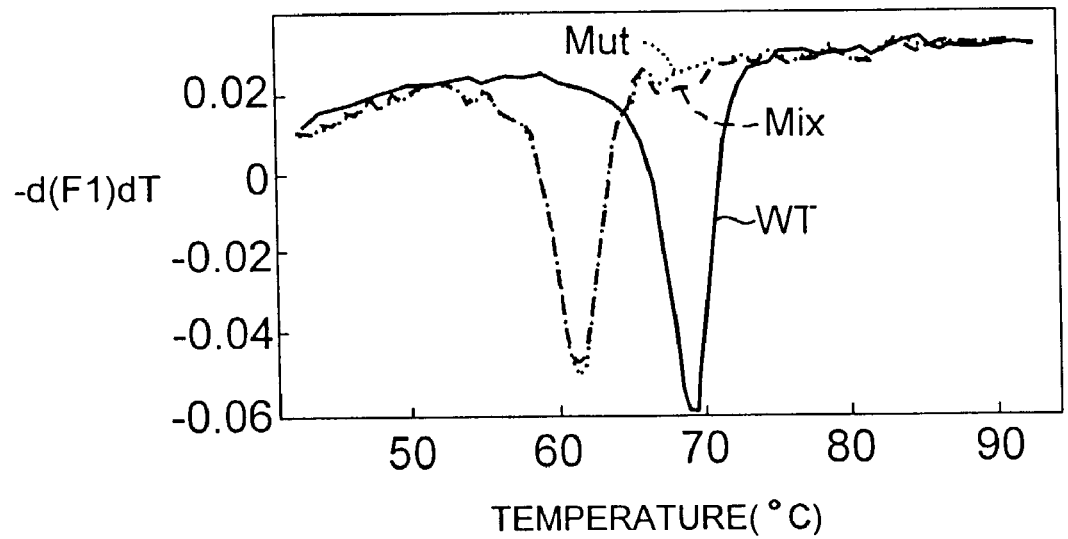
Figure 17C:
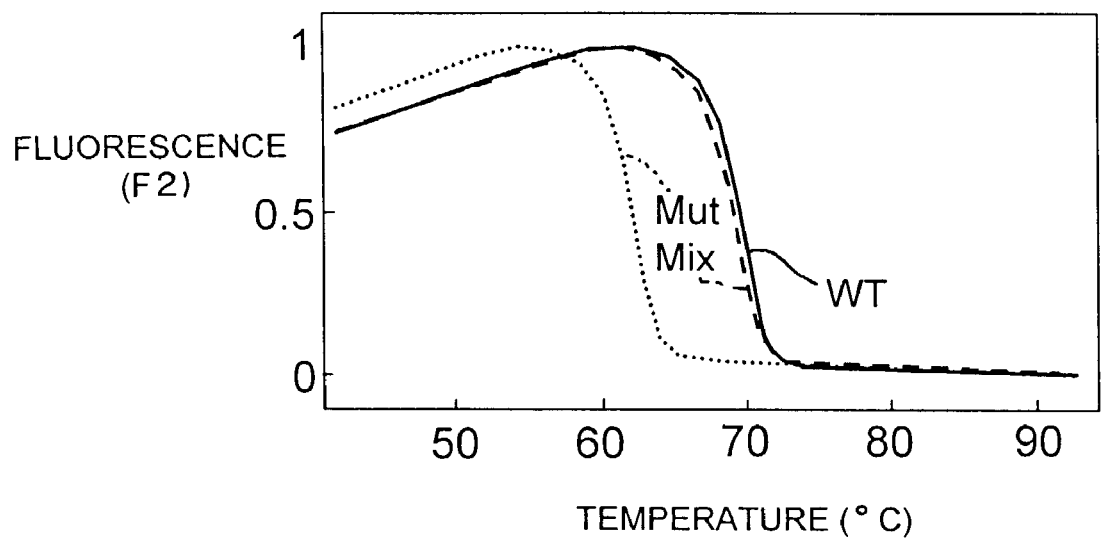
Figure 17D:
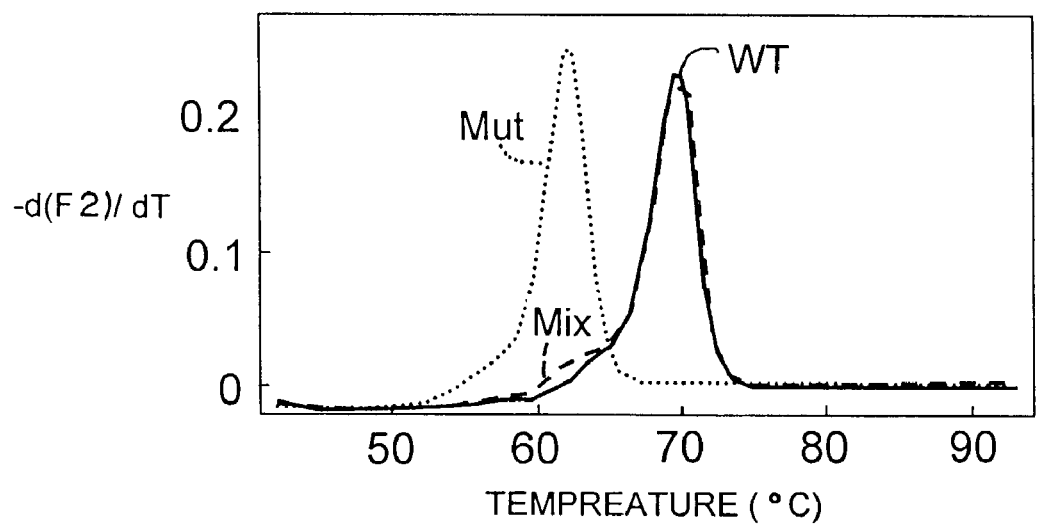

The bottom three boxes form the iterative algorithm to find all the components of the unknown. First the minimization problem defined in this section is solved for the current set of standards and remainders. Then the model is compared against the unknown, and if the fit is within a tolerance limit, the algorithm stops and reports its results. If the fit is not within the tolerance limit, then the algorithm determines a new standard and repeats the solution of the minimization problem Results The wild-type allele fraction is estimated (as "Output") using (1) the Thermodynamic Modeling Based Signal Processing (TMBSP) method, and (2) the melting peak area ratio analysis method by use of the LCDA software. In Tables 3 and 4, those outputs are compared against the actual allele fraction in the sample ("Input"). Output of TMBSP analysis is obtained for all allele fractions regardless of the probe system used. The values agree well with the Input values. Output of melting peak area ratio analysis is obtained only for the FRET pair probes in which allele fractions are greater than 10% and lower than 90% (Table 3). The LCDA software used for this analysis was unable to provide the melting peak area ratio for the Sensor probe-only system due to the opposite direction of signal change in the melting curve data (FIGS. 16b, 17b). The LCDA software is also not able to detect allele fractions of 10% and lower, or 90% and greater.

TABLE 3

| Data obtained using Sensor probe only | | |
|---|---|---|
| Input fraction of wild-type allele (%) | Output of melting peak area ratio analysis (%) | Output of TMBSP analysis (%) |
| 2 | — | 2 |
| 5 | — | 5 |
| 10 | — | 11 |
| 20 | — | 20 |
| 50 | — | 49 |
| 80 | — | 78 |
| 90 | — | 85 |
| 95 | — | 92 |
| 98 | — | 94 |

TABLE 4

| Data obtained using FRET pair (Sensor and Acceptor) probes | | |
|---|---|---|
| Input fraction of wild-type allele (%) | Output of melting peak area ratio analysis (%) | Output of TMBSP analysis (%) |
| 2 | — | 3 |
| 5 | — | 7 |
| 10 | 7 | 14 |
| 25 | 16 | 24 |
| 33 | 29 | 34 |
| 40 | 33 | 39 |
| 50 | 47 | 52 |
| 60 | 56 | 61 |
| 66 | 67 | 70 |
| 80 | 78 | 80 |
| 90 | — | 87 |
| 95 | — | 92 |
| 98 | — | 95 |

Figure 19:
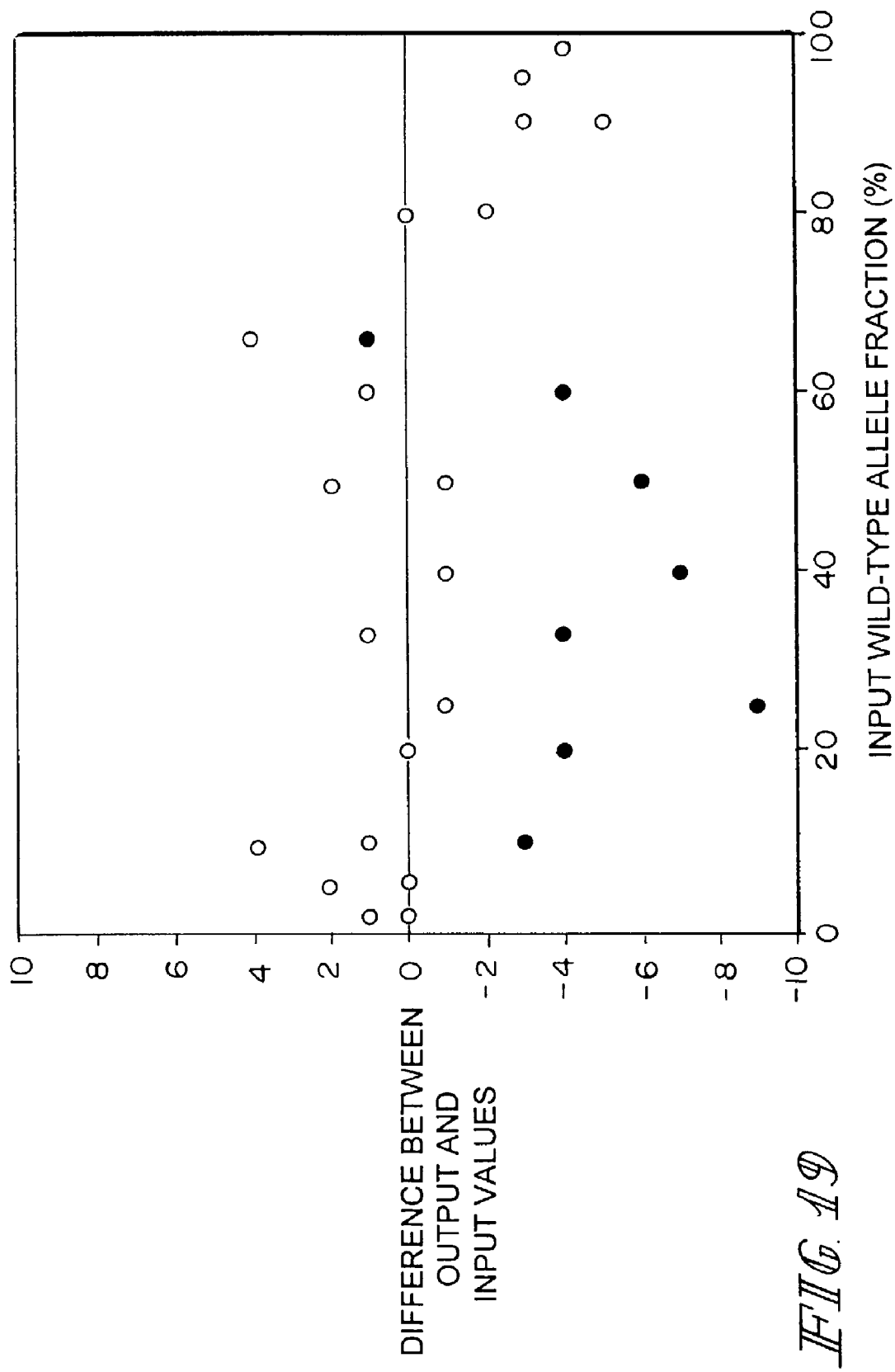
FIG. 19: is a plot of Input (the actual fraction of the wild-type allele in samples) vs the difference between Input and Output (the fractions estimated by the analysis software). Results from the Thermodynamic Modeling based Signal Processing algorithm (open circle), and the melting peak area ratio software (closed circle) are shown.

The difference between Output and Input values are plotted against the Input value (FIG. 19). A difference of zero indicates complete concordance between Output and Input values. The difference between Input, and Output using the TMBSP method has a mean of −0.15 (SD=2.4), and the confidence interval at 95% includes zero, indicating the high accuracy of estimations generated by the TMBSP algorithm. The mean difference between Input, and Output using the melting peak area ratio analysis is −4.2 (SD=2.9). The 95% confidence interval does not include zero, indicating a bias with the melting peak area ratio method.

EXAMPLE 7

This example demonstrates that the gene dosage in a mixture can be quantified using the Thermodynamic Modeling based Signal Processing (TMBSP) algorithm.

In an exemplary system, a gene locus of interest is studied for deletion or duplication using the addition of a known amount of non-amplifiable competitor DNA prior to PCR. After PCR, dosage ratio between the gene locus and the competitor in a wild type sample is compared against the ratio in unknown samples by aid of the algorithm. For instance, deletions and duplications at the exon level are known to exist in tumor suppressor genes, and while they are considered important in a variety of tumors, including breast cancer, bladder cancer, and hereditary non-polyposis colorectal cancers, detailed studies of these large deletions and duplications have been difficult due to limitations of conventional analytical methods. In this exemplary system, analysis of such large deletions or duplications is facilitated.

PCR primers are selected to amplify a segment of the gene locus of interest. Typically, the segment is 100 to 200 bp in length, although the segment can be longer or shorter. A sequence specific probe system, for example a set of hybridization probes, or alternatively, a single-labeled probe, that is complementary to a portion of the amplified segment is provided. Illustratively, this segment is void of known single nucleotide polymorphisms. In addition, a single-stranded competitor polynucleotide, also generally complementary to the probe(s) but mismatched at one or more bases, is provided. This competitor strand is illustratively shorter than the amplified segment, typically 50 to 60 bases, and lacks the region required for primer hybridization, so the competitor does not amplify during PCR. Also, the 3' end of the competitor is phosphorylated to suppress self-priming. For a typical reporter probe that is 17 to 19 bases long, a single base mismatch and/or an additional one base deletion on the competitor strand creates a 10 to 12° C. shift in melting temperature (Tm). With such a change to the competitor sequence, the competitor and the target of interest may be differentiated by Tm. Alternatively, the probe can be designed to match the competitor fully (with a mismatch to the target).

Illustratively, 1 µM of competitor is added to 10 ng of human genomic DNA in a 10 µL PCR reaction mixture that contains 0.1 to 0.2 µM of primers and other reagents for amplification. The probe(s) are also provided at a concentration of 0.2 µM.

After PCR, melting curve analysis is performed on samples that all contain the same known amount of competitor. Typically, it is not necessary to start the melting curve analysis at the exponential phase of PCR Amplified material produced after 40 to 45 cycles of PCR, and thus in the plateau phase, will provide adequate data. Two tiers of standards are used: the first tier comprises 1) a wild type sample without the competitor and 2) the competitor by itself; the second tier comprises the wild type sample mixed with the competitor. From melting curves of the first tier standards, the TMBSP algorithm computes the ratio of gene locus to the competitor in the mixed wild type standard. Unknown samples are then similarly analyzed and normalized to the ratio in the wild type. Samples that are wild type have a normalized ratio of 1.0. Samples in which the locus of interest is deleted in one chromosome (but not in the other) have a normalized ratio of 0.5. Samples with a one-fold duplication of the locus in one chromosome have a normalized ratio of 1.5.

EXAMPLE 8

The exemplary system in Example 7 is further modified to accommodate situations in which the amount of sample DNA prior to PCR is not controlled. The use of a housekeeping gene to normalize the amount of DNA across samples is well known. A second set of probes for the housekeeping gene, preferably labeled with a dye of different fluorescent color than the first set of probes, and a second competitor for the housekeeping gene in exactly the same amount as the first competitor, are added to the sample. Alternatively, a chimerical competitor carrying the sequences of the first and second competitors is used to ensure equal dosage of the two competitor sequences. The ratio of the housekeeping gene versus the competitor is calculated by use of the algorithm in all samples, and then used to normalize the dosage of the gene locus.

EXAMPLE 9

The system described in Example 7 is further simplified by the additional use of the basis function approximation algorithm (detailed in Example 6). In this case, only one standard melting curve is required. The approximation algorithm takes the melting curve of the wild type sample that is mixed with its competitor, and separates the curve into two standard curves (one for the gene alone and the other for the competitor alone). The ratio of gene locus to competitor in the wild type sample is assigned 1.0. The algorithm-generated standard curves are then used to calculate the ratios in unknown samples using the TMBSP algorithm. The final answers are the same as those generated in Example 7.

EXAMPLE 10

This example demonstrates that the mass fraction (or molar ratio) of two or more nucleic acids in a biological sample can be quantified using the Thermodynamic Modeling based Signal Processing (TMBSP) algorithm without limitation to use of the same PCR primer set for amplification, or the same probe sets for the different nucleic acids.

Segments of the human HER-2/neu gene and the housekeeping gene beta-actin are amplified using separate PCR primers for each gene, and melting analysis is performed also using separate probes. The probes are fluorescently labeled to allow detection of both genes by one detection channel on the LIGHTCYCLER® instrument. The probes also have different melting temperatures (Tm) so that the two genes can be distinguished. Example 4 describes the HER-2/neu probes in which the LCRed 640 dye is used on the reporter probe that has a Tm of 64° C. U.S. Pat. No. 6,174,670, herein incorporated by reference, describes beta-actin probes in which the reporter probe is labeled with Cy5 and has a $T_m$ of about 74° C. (U.S. Pat. No. 6,174,670 SEQ ID NO:3 and SEQ ID NO:4). The melting curve data from the wild type standard is first analyzed by the basis function approximation algorithm to convert the data into two separate melting curves. Then the ratio of Her-2/neu to beta-actin in other samples is calculated by the TMBSP algorithm, using the ratio in the wild type standard as 1.0. It is also contemplated that using similar approaches, mass fractions (or molar ratio) of more than two nucleic acid species can be quantified in a biological sample.

Although the invention has been described in detail with reference to preferred embodiments, variations and modifications exist within the scope and spirit of the invention as described and defined in the following claims.

The invention claimed is:

1. A method of determining mass fractions of first and second target nucleic acids present in a test sample comprising:
   obtaining an approximated standard melting signal, $f_i$, for each of the first and second target nucleic acids, the approximated standard melting signal for the first target nucleic acid corresponding to a change in fluorescence of the first target nucleic acid over temperature and the approximated standard melting signal for the second target nucleic acid corresponding to a change in fluorescence of the second target nucleic acid over temperature,
   contacting the target nucleic acids in the test sample with a fluorescent nucleic acid indicator, the indicator being configured to provide a signal related to the quantity of indicator hybridized to the target nucleic acids, the indicator further configured to discriminate the target nucleic acids based on melting temperature,
   illuminating the test sample including the fluorescent nucleic acid indicator,
   cycling the illuminated test sample through an annealing temperature and a denaturing temperature that is higher than the annealing temperature,
   monitoring fluorescent change of the illuminated test sample while changing temperature of the illuminated test sample to obtain a fluorescence melting signal, $f_{mix}$, of the test sample, the fluorescence melting signal, $f_{mix}$, corresponding to a change in fluorescence of the test sample over temperature, and
   approximating the fluorescence melting signal, $f_{mix}$, for the test sample over temperature, T, as a combination of the approximated standard melting signals, $f_i$, of the first and second target nucleic acids, and using $f_i$ and $f_{mix}$ to determine the mass fractions, $m_i$, of the first and second target nucleic acids in the test sample according to the formula $$\int_{T_0}^{T_1} \left\| f_{mix} - \sum_i m_i f_i(T) \right\| dT.$$

2. The method of claim 1 wherein the step of cycling the illuminated test sample through an annealing temperature and a denaturing temperature comprises:
   raising the temperature of the illuminated test sample from the annealing temperature to the denaturing temperature,
   holding the illuminated test sample at the denaturing temperature for a predetermined amount of time,
   lowering the temperature of the illuminated test sample from the denaturing temperature to a temperature that is at least as low as the annealing temperature, and
   holding the illuminated test sample at the temperature that is at least as low as the annealing temperature for at least a predetermined length of time.

3. The method of claim 2 wherein the step of cycling the illuminated test sample through an annealing temperature and a denaturing temperature further comprises thermocycling the illuminated test sample by executing the raising, lowering and both holding steps a predetermined number of times.

4. The method of claim 1 wherein the step of cycling the illuminated test sample through an annealing temperature and a denaturing temperature further comprises cycling the illuminated test sample through the annealing and denaturing temperatures for a predetermined number of repetitions.

5. The method of claim 1 wherein the step of cycling the illuminated test sample through an annealing temperature and a denaturing temperature further comprises cycling the illuminated test sample through the annealing temperature, the denaturing temperature and an elongation temperature for a predetermined number of repetitions.

6. The method of claim 1 wherein the step of monitoring fluorescent change comprises monitoring fluorescent change of the illuminated test sample once during each cycling of the illuminated test sample through the annealing temperature and the denaturing temperature.

7. The method of claim 1 wherein the step of monitoring fluorescent change comprises monitoring fluorescent change of the illuminated test sample continuously during cycling of the illuminated test sample through the annealing temperature and the denaturing temperature.

8. The method of claim 1 further comprising
   approximating a fluorescence melting signal of a PCR reaction for each additional species that does not have an approximated standard melting signal, and
   iteratively processing each of the approximated fluorescence melting signals to determine approximate standard melting signals to determine mass fractions of the additional species that do not have approximated standard melting signals according to a fit coupled thermodynamic and signal processing model.

9. The method of claim 8 wherein the iteratively processing step comprises:
   solving the fit coupled thermodynamic and signal processing model using each of the approximated fluorescence melting signals and the approximate standard melting signals to obtain a solution,
   determining whether the solution to the fit coupled thermodynamic and signal processing model is minimized, and
   defining another approximated standard melting signal based on the solution and re-executing the solving step if the solution to the fit coupled thermodynamic and signal processing model is not minimized.

10. The method of claim 9 wherein the step of determining whether the solution to the fit coupled thermodynamic and signal processing model is minimized includes:
    computing a sum of the mass fractions of the first and second target nucleic acids,
    comparing the sum of the mass fractions to a difference 1-ϵ, where ϵ is a tolerance value, and
    determining that the solution to the fit coupled thermodynamic and signal processing model is minimized if the sum of the mass fractions is greater than 1-ϵ.

11. The method of claim 9 wherein the fit coupled thermodynamic and signal processing model is defined by $$\int_{T_0}^{T_1} \left\| f_{mix}^{\sigma} - \sum_i m_i f_i^{\sigma}(T) - f^r(T) \right\| dT,$$

wherein σ is a smoothing parameter, $f^{\circ}_{mix}$ represents each of the number of fluorescence melting signals that do not have approximated standard melting signals and that are greater than σ, $m_i$ is the mass fraction of each of the first and second target nucleic acids, $f^{\circ}_i$ represents the approximated standard melting signals, and $f^r(T)$ represents the approximated fluorescence melting signals.

12. The method of claim 1 wherein the mass fractions of the first and second target nucleic acids provides information concerning a deletion or duplication in a gene.

13. The method of claim 1 wherein the fluorescent nucleic acid indicator comprises a fluorescently-labeled sequence specific oligonucleotide probe.

14. The method of claim 13 wherein the sequence specific oligonucleotide probe is selected from the group consisting of a fluorescence resonance energy transfer pair probe system and a single-labeled oligonucleotide.

15. The method of claim 1 wherein the second target nucleic acid is a competitor of the first target nucleic acid for the fluorescent nucleic acid indicator.

16. The method of claim 1 wherein the test sample further comprises a thermostable polymerase and a pair of oligonucleotide primers configured to amplify the first target nucleic acid.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Synthesized sequence for cloning.

<400> SEQUENCE: 1
```

```
ggggatccac ttcagtattg c                                              21
```

<210> SEQ ID NO 2
<211> LENGTH: 29
<212> TYPE: DNA
<213> ORGANISM: Artificial Sequence
<220> FEATURE:
<223> OTHER INFORMATION: Synthesized sequence for cloning.

<400> SEQUENCE: 2

```
gggaattcca tggctgatcc tgcaggtac                                      29
```

<210> SEQ ID NO 3
<211> LENGTH: 59
<212> TYPE: DNA
<213> ORGANISM: Artificial Sequence
<220> FEATURE:
<223> OTHER INFORMATION: Synthesized sequence for cloning.

<400> SEQUENCE: 3

```
gatcctgcag gtaccgatcg gatagtgagc gagagatagg tagggatggt tttatgtag     59
```

<210> SEQ ID NO 4
<211> LENGTH: 27
<212> TYPE: DNA
<213> ORGANISM: Artificial Sequence
<220> FEATURE:
<223> OTHER INFORMATION: Synthesized sequence for detection of
      internal quantification standard.
<220> FEATURE:
<221> NAME/KEY: misc_feature
<222> LOCATION: (1)..(1)
<223> OTHER INFORMATION: 5'-LC640 Fluorescent label

<400> SEQUENCE: 4

```
ctacctatct ctcgctcact atccatc                                        27
```

<210> SEQ ID NO 5
<211> LENGTH: 27
<212> TYPE: DNA
<213> ORGANISM: Artificial Sequence
<220> FEATURE:
<223> OTHER INFORMATION: Synthesized sequence for detection of
      artificial HPV 16 sequence.
<220> FEATURE:
<221> NAME/KEY: misc_feature
<222> LOCATION: (1)..(1)
<223> OTHER INFORMATION: 5'-LC705 Fluorescent label

<400> SEQUENCE: 5

```
attacatccc gtaccctctt ccccatt                                        27
```

<210> SEQ ID NO 6
<211> LENGTH: 22
<212> TYPE: DNA
<213> ORGANISM: Artificial Sequence
<220> FEATURE:
<223> OTHER INFORMATION: Synthesized sequence for cloning.

<400> SEQUENCE: 6

```
ccatggctga tcctgcaggt ac                                             22
```

<210> SEQ ID NO 7
<211> LENGTH: 22
<212> TYPE: DNA
<213> ORGANISM: Artificial Sequence
<220> FEATURE:
<223> OTHER INFORMATION: Synthesized sequence for cloning.

```
<400> SEQUENCE: 7
ccacttcagt attgccatac cc                                              22

<210> SEQ ID NO 8
<211> LENGTH: 59
<212> TYPE: DNA
<213> ORGANISM: Artificial Sequence
<220> FEATURE:
<223> OTHER INFORMATION: Synthesized sequence for detection of internal
      quantification standard and artificial HPV sequence.
<220> FEATURE:
<221> NAME/KEY: misc_feature
<222> LOCATION: (59)..(59)
<223> OTHER INFORMATION: 3'-fluoresein Fluorescent label

<400> SEQUENCE: 8
ctcgtcatct gatatagcat cccctgtttt tttttccact acagcctcta cataaaacc      59

<210> SEQ ID NO 9
<211> LENGTH: 23
<212> TYPE: DNA
<213> ORGANISM: Homo sapiens
<220> FEATURE:
<221> NAME/KEY: misc_feature
<222> LOCATION: (23)..(23)
<223> OTHER INFORMATION: 3'-fluoresein Fluorescent label

<400> SEQUENCE: 9
gttcctgcat gggcggcatg aac                                             23

<210> SEQ ID NO 10
<211> LENGTH: 33
<212> TYPE: DNA
<213> ORGANISM: Homo sapiens
<220> FEATURE:
<221> NAME/KEY: misc_feature
<222> LOCATION: (1)..(1)
<223> OTHER INFORMATION: 5'-LC640 Fluorescent label

<400> SEQUENCE: 10
ggaggcccat cctcaccatc atcacactgg aag                                  33

<210> SEQ ID NO 11
<211> LENGTH: 18
<212> TYPE: DNA
<213> ORGANISM: Homo sapiens

<400> SEQUENCE: 11
gcgcactggc ctcatctt                                                   18

<210> SEQ ID NO 12
<211> LENGTH: 17
<212> TYPE: DNA
<213> ORGANISM: Homo sapiens

<400> SEQUENCE: 12
ggtcagcggc aagcaga                                                    17
```